(12) United States Patent
Lovelace et al.

(10) Patent No.: US 11,291,728 B2
(45) Date of Patent: Apr. 5, 2022

(54) ANHYDROUS SODIUM THIOSULFATE AND FORMULATIONS THEREOF

(71) Applicant: Fennec Pharmaceuticals, Inc., Research Triangle Park, NC (US)

(72) Inventors: Thomas Claiborne Lovelace, Apex, NC (US); Joseph Alexander Moore, III, Wake Forest, NC (US); Christopher McKinnon Lee, Holly Springs, NC (US); Daniel Logan Kirschner, Raleigh, NC (US)

(73) Assignee: FENNEC PHARMACEUTICALS, INC., Research Triangle Park, NC (US)

( * ) Notice: Subject to any disclaimer, the term of this patent is extended or adjusted under 35 U.S.C. 154(b) by 0 days.

(21) Appl. No.: 17/005,997

(22) Filed: Aug. 28, 2020

(65) Prior Publication Data

US 2021/0015923 A1 Jan. 21, 2021

Related U.S. Application Data

(63) Continuation of application No. 16/458,261, filed on Jul. 1, 2019, now Pat. No. 10,792,363.

(60) Provisional application No. 62/693,503, filed on Jul. 3, 2018, provisional application No. 62/693,502, filed on Jul. 3, 2018.

(51) Int. Cl.
*A61K 47/20* (2006.01)
*A61K 33/243* (2019.01)
*A61K 9/00* (2006.01)
*A61K 9/08* (2006.01)
*A61K 33/04* (2006.01)
*A61K 47/02* (2006.01)
*A61K 47/18* (2017.01)

(52) U.S. Cl.
CPC ............ *A61K 47/20* (2013.01); *A61K 9/0019* (2013.01); *A61K 9/08* (2013.01); *A61K 33/04* (2013.01); *A61K 33/243* (2019.01); *A61K 47/02* (2013.01); *A61K 47/18* (2013.01); *A61K 47/183* (2013.01)

(58) Field of Classification Search
CPC ........ C01B 17/64; A61K 47/02; A61K 33/00; A61K 33/04; A61K 33/243; A61K 47/20
See application file for complete search history.

(56) References Cited

U.S. PATENT DOCUMENTS

| | | |
|---|---|---|
| 2,763,531 A | 9/1956 | Levenson |
| 7,022,315 B2 | 4/2006 | Neuwelt et al. |
| 7,276,477 B2 | 10/2007 | Osslund et al. |
| 8,496,973 B2 | 7/2013 | Sherman et al. |
| 8,710,191 B2 | 4/2014 | Gladue et al. |
| 8,715,746 B2 | 5/2014 | Sherman et al. |
| 9,144,580 B2 | 9/2015 | Sherman et al. |
| 9,345,724 B2 | 5/2016 | Sherman et al. |
| 9,579,345 B2 | 2/2017 | Sherman et al. |
| 9,732,071 B2 | 8/2017 | Patron et al. |
| 9,944,524 B2 | 4/2018 | Sherman et al. |
| 10,596,190 B2 | 3/2020 | Neuwelt |
| 2006/0177523 A1 | 8/2006 | Neuwelt et al. |
| 2014/0302179 A1* | 10/2014 | Sherman .................. A61P 9/00 424/711 |
| 2017/0056347 A1 | 3/2017 | Glick et al. |
| 2017/0129779 A1 | 5/2017 | Sherman et al. |
| 2019/0160094 A1 | 5/2019 | Neuwelt |
| 2020/0038436 A1 | 2/2020 | Neuwelt |

FOREIGN PATENT DOCUMENTS

| | | |
|---|---|---|
| GB | 713559 A | 8/1954 |
| WO | 2019108592 A2 | 6/2019 |

OTHER PUBLICATIONS

Bouffet, Eric, "Reducing cisplatin ototoxicity in children: some hope and many questions," The Lancet Oncol. 18(1): p. 6-7 (2017); doi.org/10.1016/S1470-2045(16)30630-1; Published: Nov. 30, 2016.
Brock et al., "Platinum-Induced Ototoxicity in Children: A Consensus Review on Mechanisms, Predisposition, and Protection, Including a New International Society of Pediatric Oncology Boston Ototoxicity Scale", J. Clin. Onco. 30(19):2408-2417 (2012); DOI: 10.1200/JCO.2011.39.1110; Published online Apr. 30, 2012.
Freyer et al., "Effects of sodium thiosulfate versus observation on development of cisplatin-induced hearing loss in children with cancer (ACCL0431): a multicentre, randomised, controlled, open-label, phase 3 trial," The Lancet Oncol. 18(1): p. 63-74 (2017); doi.org/10.1016/S1470-2045(16)30625-8; Published: Nov. 30, 2016.
Frisina, et al., "Comprehensive Audiometric Analysis of Hearing Impairment and Tinnitus After Cisplatin-Based Chemotherapy in Survivors of Adult-Onset Cancer," J. Clin. Oncol. 34(23):2712-2720 (2015). doi: 10.1200/JCO.2016.66.8822. Epub Jun. 27, 2016.
Gurney and Bass, "New International Society of Pediatric Oncology Boston Ototoxicity Grading Scale for Pediatric Oncology: Still Room for Improvement" J. Clin. Onc. 30(19):2303-2306 (2012); DOI: 10.1200/JCO.2011.41.3187; Published online Apr. 30, 2012.
Gurney et al., "Evaluation of amifostine for protection against cisplatin-induced serious hearing loss in children treated for average-risk or high-risk medulloblastoma," Neuro-Oncology 16(6), 848-855 (2014) doi:10.1093/neuonc/not241 Advance Access date Jan. 10, 2014.
Neuwelt et al., "First Evidence of Otoprotection Against Carboplatin-Induced Hearing Loss with a Two-Compartment System in Patients with Central Nervous System Malignancy Using Sodium Thiosulfate," J. Pharmacol. Exper. Therap. 286(1):77-84 (1998).

(Continued)

*Primary Examiner* — Timothy C Vanoy
(74) *Attorney, Agent, or Firm* — Knowles Intellectual Property Strategies, LLC

(57) ABSTRACT

Described herein is anhydrous sodium thiosulfate, methods for synthesizing anhydrous sodium thiosulfate, pharmaceutical compositions thereof, and methods of treating ototoxicity. Anhydrous sodium thiosulfate is synthesized from sodium sulfite, sulfur, and cetylpyridinium chloride. The anhydrous sodium thiosulfate is formulated into a pharmaceutical composition comprising a buffer and solvent. These compositions are useful for eliminating or reducing ototoxicity in pediatric patients receiving platinum based chemotherapeutics.

9 Claims, 6 Drawing Sheets

(56) References Cited

OTHER PUBLICATIONS

Neuwelt et al., "In Vitro and Animal Studies of Sodium Thiosulfate as a Potential Chemoprotectant against Carboplatin-induced Ototoxicity", Cancer Res. 56(5):706-709 (1996).

Neuwelt et al., "Toxicity Profile of Delayed High Dose Sodium Thiosulfate in Children Treated with Carboplatin in Conjunction with Blood-Brain-Barrier Disruption," Pediatr Blood Cancer 47(2):174-182 (2006) doi.org/10.1002/pbc.20529 First published: Aug. 5, 2005.

Pussegoda et al., Replication of TPMT and ABCC3 Genetic Variants Highly Associated With Cisplatin-Induced Hearing Loss in Children, Clin. Pharmacol. Ther. 94(2):243-251 (2013); doi: 10.1038/clpt.2013.80; Published online Apr. 10, 2013.

Ross et al. "Genetic variants in TPMT and COMT are associated with hearing loss in children receiving cisplatin chemotherapy," Nat. Genet. 41(12):1345-1349 (2009); doi: 10.1038/ng.478. Epub Nov. 8, 2009.

Xu et al., "Common variants in ACYP2 influence susceptibility to cisplatin-induced hearing loss", Nat. Genetics. 47(3):263-266 (2015); doi: 10.1038/ng.3217. Epub Feb. 9, 2015.

International Search Report and Written Opinion of the ISA dated Sep. 20, 2019, prepared in International Application No. PCT/US2019/040052.

International Search Report and Written Opinion of the ISA dated Nov. 20, 2019, prepared in International Application No. PCT/US2019/040051.

Pubchem, Substance Record SID 24880083, Sodium thiosulfate, >=99.99% trace metals basis, Available Date: Mar. 14, 2018 [retrieved on Oct. 15, 2019]. Retrieved from the Internet: <URL: https://pubchem.ncbi.nlm.nih.gov/substance/24880083>. entire document.

American Society of Health-System Pharmacists, Cisplatin, Antineoplastic Agents, AHFS Drug Information, 19 pages, 2004.

Benda, Heike von, et al., On Polymorphism of $Na_2S_2O_2$, 957-968, Translation, 1979.

Bernstein, Joel, "Analytical techniques for studying and characterizing polymorphs," Polymorphism in Molecular Crystals, Oxford University, Feb. 12, 2017, 91 pages.

Brock, Penelope, et al., "Anti-tumor efficacy in SIOPEL6: A multi-centre open label randomized phase III trial of the efficacy of sodium thiosulfate (STS) in reducing ototoxicity in patients receiving cisplatin (Cis) monotherapy for standard risk hepatoblastoma (SR-HB)." Poster Presentation, ASCO Annual Meeting, May 29-Jun. 2, 2015, 2 pages.

Brock, P. et al., "Anti-tumor efficacy in SIOPEL6: A multi-centre open label randomized phase III trial of the efficacy of sodium thiosulphate (STS) in reducing ototoxicity in patients receiving cisplatin (Cis) monotherapy for standard risk hepatoblastoma (SR-HB)." Journal of Clinical Oncology 33, No. 15_suppl (May 20, 2015).

Brock, Penelope R., et al. "Platinum-Induced Ototoxicity in Children: A Consensus Review on Mechanisms, Predisposition, and Protection, Including a New International Society of Pediatric Oncology Boston Ototoxicity Scale," Journal of Clinical Oncology, vol. 30, No. 19, Jul. 1, 2012, 10 pages.

Brock et al., "SIOPEL 6: A multi-centre open label randomized phase III trial of the efficacy of Sodium Thiosulphate in reducing ototoxicity in patients receiving cisplatin chemotherapy for standard risk hepatoblastoma," J Clin Oncol 34, 2016 (suppl; abstr 10514) Jun. 2-5, 2016.

Brock, PR, et al. Sodium thiosulfate for protection from cisplatin-induced hearing loss, SIOPEL 6, International Society of Pediatric Oncology, Protocol, 2007.

Brock, P.R., "Sodium thiosulfate for protection from cisplatin-induced hearing loss," The New England Journal of Medicine, 378:25, Jun. 21, 2018, p. 10.

Brock Powerpoint Presentation, "SIOPEL 6: A multi-centre open label randomized phase III trial of the efficacy of Sodium Thiosulphate in reducing ototoxicity in patients receiving cisplatin chemotherapy for Standard Risk Hepatoblastoma, International Childhood Liver Tumor Strategy Group"—Presented at 2016 ASCO Meeting held Jun. 2-5.

Chabner, Bruce A. et al., "Cancer Chemotherapy and Biotherapy: Principles and Practice," Fifth Edition, Wolters Kluwer Lippincott Williams & Wilkins, pp. 16, 2011.

Dasari, Shaloam, et al. "Cisplatin in Cancer Therapy: Molecular Mechanisms of Action," Eur J Pharmacol. Oct. 5, 2014; 740: 364-378. doi:10.1016/j.ejphar.2014.07.025., HHS Public Assess, 33 pages.

Dedon, Peter C. et al. "Characterization of the reasctions of platinum antitumor agents with biologic and nonbiologic sulfur-containing nucleophiles," Biochemical Pharmacology, vol. 36, No. 12, pp. 1955-1964, 1987.

Driscoll, James J., et al. "Overall Survival: Still the Gold Standard, Why Overall Survival Remains the Definitive End Point in Cancer Clinical Trials," Review Article, The Cancer Journal, vol. 15, No. 5, Sep./Oct. 2009, 401-405.

Earhart, "Instability of *cis*-Dichlorodiammineplatinum in Dextrose Solution," Cancer Treatment Reports vol. 6,2 No. 7, Jul. 1978, pp. 2.

Edwards, D.A., et al., Hydrates of Sodium Thiosulphate, Polyhedron vol. 4, No. 3, pp. 513-516, 1985, Pergamon Press Ltd.

Elferink, F., et al., Interaction of Cisplatin and Carboplatin and Sodium Thiosulfate: Reaction Rates and Protein Binding, Clin. Chem. 32/4, 641-645 (1986).

FENNEC 2015 Annual Report, Mar. 28, 2016, 60 pages.

Freyer, David et al. "Effects of sodium thiosulfate versus observation on development of cisplatin-induced hearing loss in children with cancer (ACCL0431): a multicentre, randomised, controlled, open-label, phase 3 trial," vol. 18, Jan. 2017, 12 pages.

Freyer, David, "The effects of sodium thiosulfate (STS) on cisplatin-induced hearing loss: A report from the Children's Oncology Group." J Clin Oncol 32:5s, (suppl; abstr 10017), 2014.

Galluzzi, L. et al., "Molecular mechanisms of cisplatin resistance," Oncogene (2012) 31, 1869-1883, Macmillan Publishers Limited.

Gurney, James G., et al., "Hearing loss, quality of life, and academic problems in long-term nuroblastoma survivors: A report from the children's oncology group," Pediatrics, vol. 120, No. 5, Nov. 1007, e1229, pp. 10.

Gurney, H., "How to calculate the dose of chemotherapy," British Journal of Cancer (2002) 86, 1297-1302 Cancer Research UK, pp. 6.

Harned et al., Sodium Thiosulfate Administered Six Hours After Cisplatin Does Not Compromise Antineuroblastoma Activity. Clin. Cancer Res. 2008; 14(2), Jan. 15, 2008.

Jaszczak-Figiel Beata, et al., "Stages of thermal decomposition of sodium oxosalts of sulphur," Journal of Thermal Analysis and Calorimetry, vol. 96 (2009) 1, 147-14.

Knight, Kristin R., et al. "Ototoxicity in Children Receiving Platinum Chemotherapy: Underestimating a Commonly Occurring Toxicity That May Influence Academic and Social Development," Journal of Clinical Oncology, vol. 23, No. 34, Dec. 1, 2005.

Landier, Wendy, et al., "Ototoxicity in Children With High-Risk Neuroblastoma: Prevalence, Risk Factors, and Concordance of Grading Scales—A Report From the Children's Oncology Group," Journal of Clinical Oncology, vol. 32, No. 6, Feb. 20, 2014, pp. 13.

Li, Y., et al. "Predicting cisplatin ototoxicity in children: the influence of age and the cumulative dose," European Journal of Cancer 10 (2004) 2445-2451.

Long, D. F., et al. Cisplatin: Chemistry, distribution and bioransformation, Biopharmaceutics & Drug Disposition, vol. 2, 1-16 (1981).

IPR2022-00125 Petition for Inter Partes Review Under 37 C.F.R. § 42.100 dated Oct. 29, 2021; In the *Inter Partes*Review of U.S. Pat. No. 10,792,363.

(56) References Cited

OTHER PUBLICATIONS

IPR2022-00123 Petition for Inter Partes Review Under 37 C.F.R. § 42.100 dated Oct. 29, 2021; In the *Inter Partes*Review of U.S. Pat. No. 10,596,190.
IPR (190) Exhibit 1007 Earhart's Declaration.
IPR (190) Exhibit 1008 Garcia's Declaration.
IPR (190) Exhibit 1009 Platinol-AQ Cisplatin Insert.
IPR (190) Affidavit of Elizabeth Rosenberg, Internet Archive, 7 pages, Sep. 16, 2020.
IPR (363) Declaration Brendan Y. Keenan.
IPR (363) Declaration of Robin D. Rogers.
Muldoon, Leslie L., et al. "Delayed administration of sodium thiosulfate in animal models reduces platinum ototoxicity without reduction of antitumor activity," American Association for Cancer Research, vol. 6, 309-315, Clinical Cancer Research, Jan. 2000.
Pattanaik, Asima, et al., "Properties of the reaction of *cis*-Dichlorodiammineplatinum(II) with Metallothionein," vol. 267, No. 23, Issue of Aug. 15, pp. 16121-16128, 1992.
Presentation by David R. Freyer, "ACCL0431: a Randomized Phase III Study of Sodium thiosulfate (SYS) for Prevention of Cisplatin-induced Hearing Loss in Children" Jun. 1, 2014.
Press Release, Adherex Technologies, Inc., "Adherex Announces Results from Two Sodium Thiosulfate Phase 3 Studies Presented at the 50th American Society of Clinical Oncology (ASCO) Meeting," Jun. 2, 2014, 18 pages.
Press Release, Fennec Pharmaceuticals, Inc., "Fennec Announces Sodium Thiosulfate Presentation for Prevention of Ototoxicity in Children at ASCO Meeting," Apr. 20, 2016, 13 pages.
Press Release, Fennec Pharmaceuticals, Inc., "Fennec Announces Positive Results from Phase 3 SIOPEL 6 Study on PEDMARKTM (sodium thiosulfate) Presented at 49th Congress of the International Society of Pediatric Oncology (SIOP) 2017 Meeting," Oct. 16, 2017.
Pubchem.ncbi.nlm.nih.gov/compound/31239, Cetylpyridinium Chloride, C21H38ClN, 2021 38 pages.
Sankar, C., et al. "Intensification of solid-liquid reactions using surfactants: sulfur-sulfite reaction," Recent Trends In Chemical Reaction Engineering, vol. II, International Chemical Reaction, Bombay, India, 1987.
Sheth, Sandeep, et al. "Mechanisms of cisplatin-induced ototoxicity and otoprotection," Frontiers in Cellular Neuroscience, Springfield, IL, Article 338, Oct. 27, 2017.
The United States Pharmacopeia, The National Formulary, vol. 4, Chapter 232, 7 pages, 2018.
The United States Pharmacopeia, The National Formulary, vol. 4, Chapter 467, 18 pages 2018.
Van As Jw, et al. "Medical interventions for the prevention of platinum-induced hearing loss in children with cancer (Review)," Cochrane Database of Systematic Reviews 2016, Issue 9, DOI: 10.1002/14651858.CD009219.pub4, pp. 51.
Wang, Xiaoyong, et al., "The role of sulfur in platinum anticancer chemotherapy," Anti-Cancer Agents in Medicinal Chemistry (Formerly Current Medicinal Chemistry—Anti-Cancer Agents) 2007, 7, 19-34 19 Bentham Science Publishers Ltd.
Wood, Horatio C. et al., The Dispensatory of The United States of America, 22nd Edition (with Supplement), Philadelphia and London J.B. Lippincott Company 1940.
U.S. Pat. No. 10,792,363 B2, U.S. Appl. No. 16/458,261, Lovelace et al. dated Oct. 6, 2020.
U.S. Publication No. 2020/0023003 A1, U.S. Appl. No. 16/458,267, Lee et al., dated Jan. 23, 2020.
U.S. Appl. No. 17/584,257, Lovelace et al., filed Jan. 25, 2022.

\* cited by examiner

ANHYDROUS SODIUM THIOSULFATE AND FORMULATIONS THEREOF

CROSS-REFERENCE TO RELATED APPLICATIONS

This application is a continuation of U.S. application Ser. No. 16/458,261, filed Jul. 1, 2019, which claims benefit of U.S. Provisional Patent Application Nos. 62/693,502 and 62/693,503, both filed on Jul. 3, 2018, the entire contents of which are hereby incorporated herein by reference. Additionally, U.S. patent application Ser. No. 16/458,267, titled "FORMULATIONS OF ANHYDROUS SODIUM THIOSULFATE," filed on Jul. 1, 2019, is incorporated by reference herein in its entirety.

TECHNICAL FIELD

Described herein is anhydrous sodium thiosulfate, methods for synthesizing anhydrous sodium thiosulfate, and pharmaceutical compositions thereof. These compositions are useful for eliminating or reducing ototoxicity in patients receiving platinum-based chemotherapeutics.

BACKGROUND

Platinum based therapeutics are highly important components of treatment regimens used in a variety of pediatric malignancies including neuroblastoma, hepatoblastoma, medulloblastoma, osteosarcoma, malignant germ cell tumors, and nasopharyngeal carcinomas. At commonly used doses and schedules, platinum based therapeutics, such as cisplatin and carboplatin, frequently cause hearing loss that is progressive, bilateral, irreversible, and often accompanied by tinnitus. Platinum chemotherapeutic based hearing loss can affect all hearing frequencies owing to the death of cochlear outer hair cells.

These toxicities can be dose limiting and are often clinically significant, especially in young children who are critically dependent upon normal hearing for cognitive, psychosocial, and speech development. Approximately 40% of children develop cisplatin-induced hearing loss with nearly 100% incidence for certain vulnerable groups. The effects of even mild hearing loss in pediatrics is substantial with, inter alia, reduced language acquisition, learning, academic performance, social and emotional development, and life quality. Thus, there is a need for safe and effective pharmaceutical compositions and methods for treating pediatric patients to reduce ototoxicity and hearing loss in these patients that do not compromise the efficacy of the platinum-based therapeutic.

SUMMARY

One embodiment described herein is anhydrous sodium thiosulfate characterized by an X-ray powder diffraction (XRPD) pattern comprising at least four peaks selected from 10.52, 15.13, 17.71, 19.70, 21.09, 21.49, 21.84, 27.40, 28.96, 30.46, 31.81, 32.52, 33.15, 37.40, or 38.16 degrees 2 theta (2 θ)±0.2, when the XRPD is collected from about 2 to about 40 degrees 2 θ using copper Kα radiation. In one aspect, the anhydrous sodium thiosulfate is characterized by an X-ray powder diffraction (XRPD) pattern comprising at least four peaks selected from 10.52, 15.13, 19.70, 21.49, 21.84, 28.96, 30.46, 33.15, 37.40, and 38.16 degrees 2 theta (2 θ)±0.2, when the XRPD is collected from about 2 to about 40 degrees 2 θ using copper Kα radiation. In another aspect, the anhydrous sodium thiosulfate is characterized by a differential scanning calorimetry melting onset of about 331° C.; and a thermogravimetric analysis showing negligible weight loss from ambient temperature to 162° C., a weight loss of 14.8% from 162° C. to 309° C., and an onset of decomposition at 436° C.

Another embodiment described herein is anhydrous sodium thiosulfate comprising: no greater than 0.1 µg/g of cadmium; no greater than 0.25 µg/g lead; no greater than 0.75 µg/g arsenic; no greater than 0.15 µg/g mercury; no greater than 0.25 µg/g cobalt; no greater than 0.5 µg/g vanadium; no greater than 1.0 µg/g nickel; no greater than 12.5 µg/g lithium; no greater than 4.5 µg/g antimony; no greater than 15.0 µg/g copper; no greater than 1500 ppm methanol; no greater than 3% (w/w) water; and no greater than 1.65% (w/w) of total impurities or related substances.

Another embodiment described herein is a method for synthesizing sodium thiosulfate comprising reacting sodium sulfite with sulfur in the presence of a surface acting agent. In one aspect, the surface acting agent comprises cetylpyridinium chloride. In another aspect, the reaction is aqueous. In another aspect, the reaction is conducted at about 80° C. to about 100° C. In another aspect, the sodium thiosulfate is crystallized and washed with acetone.

Another embodiment described herein is a method for synthesizing anhydrous sodium thiosulfate comprising reacting sodium sulfite with sulfur in the presence of cetylpyridinium chloride and dehydrating sodium thiosulfate product. In one aspect, the reaction comprises 1.0 mole equivalent of sodium sulfite; 1.1 mole equivalents of sulfur; and 0.00013 mole equivalents of cetylpyridinium chloride. In another aspect, the reaction is aqueous. In another aspect, the reaction is conducted at about 80° C. to about 100° C. In another aspect, the sodium thiosulfate is crystallized and washed with acetone. In another aspect, the sodium thiosulfate is dehydrated and washed with methanol. In another aspect, the sodium thiosulfate is dried.

Another embodiment described herein is a method for synthesizing anhydrous sodium thiosulfate comprising: (a) reacting aqueous sodium sulfite with sulfur and cetylpyridinium chloride; (b) crystallizing sodium thiosulfate and washing with acetone; (c) dehydrating the washed sodium thiosulfate with methanol; and (d) drying the dehydrated sodium thiosulfate. In one aspect, the reaction comprises 1.0 mole equivalent of sodium sulfite; 1.1 mole equivalents of sulfur; and 0.00013 mole equivalents of cetylpyridinium chloride.

Another embodiment described herein is a method for synthesizing anhydrous sodium thiosulfate comprising: (a) reacting 1.0 mole equivalent of aqueous sodium sulfite with 1.1 mole equivalents of sulfur in the presence of 0.00013 mole equivalents of cetylpyridinium chloride at about 90° C. to about 100° C.; (b) crystallizing sodium thiosulfate at <2° C. and washing with acetone; (c) dehydrating the washed sodium thiosulfate with methanol; and (d) drying the dehydrated sodium thiosulfate at about 25° C. to about 60° C.

Another embodiment described herein is anhydrous sodium thiosulfate synthesized by the methods described herein.

Another embodiment described herein is a means for synthesizing anhydrous sodium thiosulfate comprising reacting sodium sulfite with sulfur in the presence of cetylpyridinium chloride, crystallizing the sodium thiosulfate product, and dehydrating sodium thiosulfate product.

Another embodiment described herein is anhydrous sodium thiosulfate synthesized by the means described herein.

Another embodiment described herein is anhydrous sodium thiosulfate comprising essentially no sodium thiosulfate pentahydrate.

Another embodiment described herein is a method for measuring the binding capacity of sodium thiosulfate for cisplatin comprising: (a) mixing one or more ratios of sodium thiosulfate with a predetermined quantity of cisplatin; (b) incubating the mixture for a period of time; and (c) analyzing the apparent concentration of cisplatin. In one aspect, the ratios of sodium thiosulfate to cisplatin comprise 10:1 to 1:1. In another aspect, the ratios of sodium thiosulfate to cisplatin comprise 10:1, 6:1, and 5:1. In another aspect, the incubation period of time comprises 1 min to 180 min. In another aspect, the incubation period of time comprises about 5 min; about 35 min, about 65 min; and about 95 min. In another aspect, the analyzing comprises HPLC and UV detection.

Another embodiment described herein is a pharmaceutical composition comprising sodium thiosulfate, one or more buffers, and a solvent. Another embodiment described herein is a pharmaceutical composition comprising anhydrous sodium thiosulfate. Another embodiment described herein is a pharmaceutical composition comprising anhydrous sodium thiosulfate. Another embodiment described herein is a pharmaceutical composition consisting essentially of anhydrous sodium thiosulfate. Another embodiment described herein is a pharmaceutical composition consisting essentially of aqueous anhydrous sodium thiosulfate.

Another embodiment described herein is a pharmaceutical composition comprising anhydrous sodium thiosulfate, and one or more buffers. Another embodiment described herein is a pharmaceutical composition consisting of anhydrous sodium thiosulfate, and one or more buffers. In one aspect, the composition comprises about 20 mg to 32 g of anhydrous sodium thiosulfate. In another aspect, the composition comprises about 98% by mass of anhydrous sodium thiosulfate. In another aspect, the composition is a dry powder. In another aspect, the composition is a lyophilized solution.

Another embodiment described herein is a pharmaceutical composition comprising aqueous anhydrous sodium thiosulfate, one or more buffers, and a solvent. Another embodiment described herein is a pharmaceutical composition consisting essentially of anhydrous sodium thiosulfate, one or more buffers, and a solvent.

Another embodiment described herein is a pharmaceutical composition comprising about 0.1 M to about 2 M of aqueous anhydrous sodium thiosulfate, 0.001 M to about 0.5 M of one or more buffers, and water. Another embodiment described herein is a pharmaceutical composition comprising about 0.1 M to about 2 M of aqueous anhydrous sodium thiosulfate, 0.01 M to about 0.5 M of sodium phosphate, pH 6.5, and water. Another embodiment described herein is a pharmaceutical composition comprising about 0.1 M to about 2 M of aqueous anhydrous sodium thiosulfate, 0.001 M to about 0.5 M of boric acid or a salt thereof, pH 8.6-8.8, and water. Another embodiment described herein is a pharmaceutical composition comprising about 0.1 M to about 2 M of aqueous anhydrous sodium thiosulfate, 0.001 M to about 0.5 M of glycine or a salt thereof, pH 8.5-8.9, and water. Another embodiment described herein is a pharmaceutical composition comprising about 0.1 M to about 2 M of aqueous anhydrous sodium thiosulfate, 0.001 M to about 0.5 M of tris(hydroxymethyl)aminomethane (tromethane) or a salt thereof, pH 8.5-8.9, and water.

Another embodiment described herein is a pharmaceutical composition comprising about 0.5 M of aqueous anhydrous sodium thiosulfate, about 0.01 M of sodium phosphate, pH 6.5, and water. Another embodiment described herein is a pharmaceutical composition comprising about 0.5 M of aqueous anhydrous sodium thiosulfate, about 0.004 M of boric acid or a salt thereof, pH 8.6-8.8, and water. Another embodiment described herein is a pharmaceutical composition comprising about 0.5 M of aqueous anhydrous sodium thiosulfate, about 0.01 M to about 0.05 M of glycine, pH 8.5-8.9, and water. Another embodiment described herein is a pharmaceutical composition comprising about 0.1 M to about 2 M of aqueous anhydrous sodium thiosulfate, 0.001 M to about 0.5 M of tris(hydroxymethyl)aminomethane (tromethane) or a salt thereof, pH 8.5-8.9, and water.

Another embodiment described herein is a pharmaceutical composition comprising aqueous anhydrous sodium thiosulfate, one or more buffers, and a solvent. In one aspect, the composition comprises about 20 mg/mL to 320 mg/mL of aqueous anhydrous sodium thiosulfate. In another aspect, the composition comprises about 8% by mass to about 32% by mass of aqueous anhydrous sodium thiosulfate. In another aspect, the composition comprises about 0.1 M to about 2 M of aqueous anhydrous sodium thiosulfate. In another aspect, the composition comprises about 0.001 M to about 0.5 M of the one or more buffers. In another aspect, the one or more buffers comprise phosphate, sulfate, carbonate, borate, formate, acetate, propionate, butanoate, lactate, glycine, maleate, pyruvate, citrate, aconitate, isocitrate, α-ketoglutarate, succinate, fumarate, malate, oxaloacetate, aspartate, glutamate, tris(hydroxymethyl)aminomethane (tromethamine), combinations thereof, or salts thereof. In another aspect, the composition has a pH of about 5 to about 9.5. In another aspect, the composition has a pH of about 6.5 or about 8.9. In another aspect, the one or more buffers comprise borate or a salt thereof, glycine or a salt thereof, tris(hydroxymethyl)aminomethane (tromethamine) or a salt thereof, or phosphate or a salt thereof. In another aspect, the one or more buffers comprise boric acid, glycine, tris(hydroxymethyl)aminomethane (tromethamine), or sodium phosphate. In another aspect, the solvent comprises water. In another aspect, the composition is sterile.

Another embodiment described herein is a pharmaceutical composition comprising about 0.1 M to about 2 M of aqueous anhydrous sodium thiosulfate, 0.001 M to about 0.5 M of sodium phosphate or boric acid. In one aspect, the composition comprises about 0.5 M of aqueous anhydrous sodium thiosulfate, and about 0.01 M of sodium phosphate, pH 6.5. In another aspect, the composition comprises about 0.5 M of aqueous anhydrous sodium thiosulfate and about 0.004 M of borate or a salt thereof, pH 8.6-8.8. In another aspect, the composition comprises about 0.5 M of aqueous anhydrous sodium thiosulfate and about 0.01 M to about 0.05 M of glycine or a salt thereof, pH 8.5-8.9. In another aspect, the composition comprises about 0.5 M of aqueous anhydrous sodium thiosulfate and about 0.01 M to about 0.05 M of tris(hydroxymethyl)aminomethane (tromethamine) or a salt thereof, pH 8.5-8.9.

Another embodiment described herein is a pharmaceutical composition comprising about 0.5 M of aqueous anhydrous sodium thiosulfate, about 0.01 M of sodium phosphate, pH 6.5, and water.

Another embodiment described herein is a pharmaceutical composition comprising about 0.5 M of aqueous anhydrous sodium thiosulfate, about 0.004 M of borate or a salt thereof, pH 8.6-8.8, and water.

Another embodiment described herein is a pharmaceutical composition comprising about 0.5 M of aqueous anhydrous sodium thiosulfate, about 0.01 M to about 0.05 M of glycine or a salt thereof, pH 8.5-8.9, and water.

Another embodiment described herein is a pharmaceutical composition comprising about 0.5 M of aqueous anhydrous sodium thiosulfate, about 0.01 M to about 0.05 M of tris(hydroxymethyl)aminomethane (tromethamine) or a salt thereof, pH 8.5-8.9, and water.

Another embodiment described herein is a method for preparing a pharmaceutical formulation comprising anhydrous sodium thiosulfate, the method comprising combining anhydrous sodium sulfate with one or more buffers and a solvent. In one aspect, the method further comprising filtering and sterilizing the formulation. In another aspect, the formulation comprises about 20 mg/mL to 320 mg/mL of aqueous anhydrous sodium thiosulfate. In another aspect, the formulation comprises about 8% by mass to about 32% by mass of aqueous anhydrous sodium thiosulfate. In another aspect, the formulation comprises about 0.1 M to about 2 M of aqueous anhydrous sodium thiosulfate. In another aspect, the formulation comprises about 0.001 M to about 0.5 M of the one or more buffers. In another aspect, the one or more buffers comprise phosphate, sulfate, carbonate, formate, acetate, propionate, butanoate, lactate, glycine, maleate, pyruvate, citrate, aconitate, isocitrate, α-ketoglutarate, succinate, fumarate, malate, oxaloacetate, aspartate, glutamate, tris(hydroxymethyl)aminomethane (tromethamine), combinations thereof, or salts thereof. In another aspect, the formulation has a pH of about 5 to about 9.5. In another aspect, the formulation has a pH of about 6.5 or about 8.9. In another aspect, the one or more buffers comprise borate or a salt thereof, glycine or a salt thereof, tris(hydroxymethyl)aminomethane (tromethamine) or a salt thereof, or phosphate or a salt thereof. In another aspect, the one or more buffers comprise sodium phosphate, glycine, or boric acid. In another aspect, the solvent comprises water. In another aspect, the formulation comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

Another embodiment described herein is a pharmaceutical formulation comprising about 0.5 M of aqueous anhydrous sodium thiosulfate, about 0.01 M of sodium phosphate, pH 6.5, and water made by the method described herein.

Another embodiment described herein is a pharmaceutical formulation comprising about 0.5 M of aqueous anhydrous sodium thiosulfate, about 0.004 M of boric acid, pH 8.6-8.8, and water made by the method described herein.

Another embodiment described herein is a pharmaceutical formulation comprising about 0.5 M of aqueous anhydrous sodium thiosulfate, about 0.01 M to about 0.05 M of glycine, pH 8.5-8.9, and water made by the method described herein.

Another embodiment described herein is a pharmaceutical formulation comprising about 0.5 M of aqueous anhydrous sodium thiosulfate, about 0.01 M to about 0.05 M of tris(hydroxymethyl)aminomethane (tromethamine), pH 8.5-8.9, and water made by the method described herein.

Another embodiment described herein is a means for preparing a pharmaceutical formulation comprising anhydrous sodium thiosulfate, the method comprising combining anhydrous sodium sulfate with one or more buffers and a solvent. Another embodiment is a pharmaceutical formulation prepared by the means described herein.

Another embodiment described herein is a pharmaceutical composition comprising an aqueous solution of about 0.2 M to about 2 M of sodium thiosulfate, about 0.001 M to about 0.05 M of a pharmaceutically acceptable buffer, and about 0.005 M to about 0.05 M of a pharmaceutically acceptable salt, and a pH of about 5 to about 9.5.

Another embodiment described herein is a kit comprising an aqueous sodium thiosulfate formulation comprising one or more receptacles comprising aqueous sodium thiosulfate; and documents comprising prescribing information or instructions for use. In one aspect, the kit further comprises one or more syringes, hypodermic needles, and packaging.

Another embodiment described herein is a kit comprising one or more receptacles comprising dry or lyophilized sodium thiosulfate; and optionally: one or more sterile solvents appropriate for reconstitution; a needle and syringe; and documents comprising prescribing information or instructions for use.

Another embodiment described herein is a pharmaceutical formulation comprising aqueous anhydrous sodium thiosulfate for injection that is stable and does not precipitate after sterilization and storage. In one aspect, the formulation comprises about 0.1 M to about 2 M of aqueous anhydrous sodium thiosulfate, 0.001 M to about 0.5 M of sodium phosphate, glycine, tris(hydroxymethyl)aminomethane (tromethamine), or boric acid.

Another embodiment described herein is a method for preventing or reducing the incidence of by cisplatin (CIS) chemotherapy induced ototoxicity in patients 1 month to <18 years of age with localized, non-metastatic, solid tumors comprising administering sodium thiosulfate for injection as a 15-minute infusion, 6 hours after the completion of each CIS administration, when CIS is infused for no longer than 6 hours.

Also described herein are compositions and methods for reducing ototoxicity in patients having received a platinum based chemotherapeutic. In particular, compositions and intravenous formulations for reducing ototoxicity in pediatric patients are described. Also described are methods for administering the compositions and formulations. The methods include administering an effective amount of sodium thiosulfate to the patient following administration of the platinum based chemotherapeutic. As described herein, the administration of sodium thiosulfate was found to not adversely affect the efficacy of the platinum based chemotherapeutic and decreased the incidence and severity of ototoxicity in pediatric patients. In one aspect, the method comprises administering a sodium thiosulfate pharmaceutical composition as described herein. In another aspect, the pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water. Another embodiment is a method of reducing ototoxicity in a patient having a cancer and receiving a platinum based chemotherapeutic comprising administering an effective amount of sodium thiosulfate to the patient.

Another embodiment is a method of prophylactically treating a patient having a cancer and receiving a platinum based chemotherapeutic to reduce a likelihood of the patient incurring ototoxicity comprising administering an effective amount of sodium thiosulfate to the patient. In one aspect, the method comprises administering a sodium thiosulfate pharmaceutical composition as described herein. In one aspect, the pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

Another embodiment is a method of reducing long term ototoxicity in a patient having a cancer and receiving a platinum based chemotherapeutic comprising administering an effective amount of sodium thiosulfate to the patient. In one aspect, the method comprises administering a sodium thiosulfate pharmaceutical composition as described herein. In another aspect, the pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

Another embodiment is a method of reducing a concentration of cisplatin in an aural cavity of a patient having a cancer and receiving a platinum based chemotherapeutic comprising administering an effective amount of sodium thiosulfate to the patient, wherein substantially no cisplatin is detectable in the aural cavity and wherein the patient administered the sodium thiosulfate is less susceptible to incurring ototoxicity from the platinum based chemotherapeutic.

Another embodiment is a method of inhibiting ototoxic effects associated with an administration of platinum-based chemotherapeutic compounds in a patient comprising administering an effective amount of sodium thiosulfate to the patient.

In some embodiments described herein, the patient carries has single nucleotide polymorphism in a gene ACYP2 at locus rs1872328. In some embodiments, the patient administered sodium thiosulfate is about 20% to about 75% less likely to experience ototoxicity than a patient not administered sodium thiosulfate. In some embodiments, the patient administered sodium thiosulfate is about 50% less likely to experience ototoxicity than a patient not administered sodium thiosulfate. In some embodiments, ototoxicity comprises hearing loss, dysequilibrium, tinnitus, hearing sensitivity, or combinations thereof.

In some embodiments described herein, the platinum based chemotherapeutic is selected from cisplatin, carboplatin, oxaliplatin, nedaplatin, triplatin tetranitrate, phenanthriplatin, picoplatin, and satraplatin. In some embodiments, the platinum based chemotherapeutic is cisplatin.

In some embodiments, the cancer being treated is localized or disseminated. In some embodiments, the cancer being treated is localized. In some embodiments, the cancer being treated is selected from a germ cell tumor, hepatoblastoma, medulloblastoma, neuroblastoma, and osteosarcoma. In some embodiments, the cancer being treated is hepatoblastoma. In some embodiments, the cancer being treated is a standard risk cancer, intermediate risk cancer, or high risk cancer. In some embodiments, the cancer being treated is a standard risk cancer or an intermediate risk cancer. In some embodiments, the cancer being treated is standard risk or intermediate risk hepatoblastoma.

In some embodiments, the sodium thiosulfate is administered prior to, concurrently with, or after the administration of the platinum based chemotherapeutic. In some embodiments, the sodium thiosulfate is administered about 0.5 hours to about 10 hours after the administration of the platinum based chemotherapeutic. In some embodiments, the sodium thiosulfate is administered intravenously. In some embodiments, the effective amount of sodium thiosulfate is from about 5 $g/m^2$ to about 25 $g/m^2$ per cycle of the platinum based chemotherapeutic. In some embodiments, the patient is being treated with a dose of about 1 mg/kg to about 5 mg/kg or about 10 $mg/m^2$ to about 300 $mg/m^2$ per cycle of the platinum based chemotherapeutic. In one aspect, sodium thiosulfate comprises a pharmaceutical composition as described herein. In another aspect, the sodium thiosulfate pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

In some embodiments described herein, ototoxicity is determined by one or more criteria comprising: a tinnitus functional index, Brock grading, American Speech-Language-Hearing Association criteria, or International Society of Pediatric Oncology Boston Ototoxicity Scale. In some embodiments ototoxicity is determined by measuring a hearing loss at one or more frequencies comprising 500 Hz, 1,000 Hz, 2,000 Hz, 4,000 Hz, or 8,000 Hz or a combination of frequencies thereof, wherein a change in hearing is computed relative to baseline measures prior to the patient receiving a platinum based chemotherapeutic or sodium thiosulfate or both.

In some embodiments described herein, ototoxicity is determined by one or more criteria comprising: (a) a reduction in hearing measured by a 20 dB loss at a single frequency; (b) a reduction in hearing measured by a 10 dB loss at two consecutive frequencies; (c) loss of response at three consecutive test frequencies where responses were previously obtained; (d) a reduction in bilateral high-frequency hearing characterized by: (i) a <40 dB hearing loss at all frequencies, which indicates a grade 0 or minimal hearing loss; (ii) a ≥40 dB hearing loss at 8,000 Hz only, which indicates a grade 1 or mild hearing loss; (iii) a ≥40 dB hearing loss at 4,000 Hz and above, which indicates a grade 2 or moderate hearing loss; (iv) a ≥40 dB hearing loss at 2,000 Hz and above, which indicates a grade 3 or marked hearing loss; (v) a ≥40 dB hearing loss at 1,000 Hz and above, which indicates a grade 4 or severe hearing loss; or (e) a reduction in hearing characterized by: (i) a ≤20 dB hearing loss at all frequencies, which indicates a grade 0 hearing loss; (ii) a >20 dB HL above 4,000 Hz, which indicates a grade 1 hearing loss; (iii) a >20 dB HL at 4,000 Hz and above, which indicates a grade 2 hearing loss; (iv) a >20 dB HL at 2,000 Hz or 3,000 Hz, which indicates a grade 3 hearing loss; (v) a >40 dB HL at 2,000 Hz and above, which indicates a grade 1 hearing loss, or (f) an improvement in a tinnitus functional index; and wherein a change in hearing is computed relative to baseline measures prior to the patient receiving a platinum based chemotherapeutic or sodium thiosulfate or both. In some embodiments, the pediatric patient administered sodium thiosulfate has a reduction in ototoxicity assessed by criterion (d) described above compared to a pediatric patient not administered sodium thiosulfate.

In some embodiments described herein, the administration of sodium thiosulfate to a patient does not lead to increased serum creatinine or a reduction in glomerular filtration rate compared to a patient not administered sodium thiosulfate. In some embodiments, the administration of sodium thiosulfate to a patient does not affect relapse free survival or overall survival compared to a patient not administered sodium thiosulfate. In some embodiments, the administration of sodium thiosulfate to a patient does not lead to increased incidence of one or more adverse events comprising febrile neutropenia, infection, hypomagnesemia, hypernatremia, vomiting, or nausea.

In some embodiments described herein, ototoxicity is measured at a time of at least 4 weeks following the administration of the platinum based chemotherapeutic and sodium thiosulfate to a patient. In one aspect, the sodium thiosulfate comprises a pharmaceutical composition as described herein. In another aspect, the sodium thiosulfate pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

In some embodiments described herein, the patient is a pediatric patient. In some embodiments described herein, the pediatric patient is 1 week of age to 18 years of age. In some embodiments, the pediatric patient is about 12 years of age or less. In some embodiments, the pediatric patient is about 5 years of age or less. In some embodiments, the pediatric patient is about 2 years of age or less. In some embodiments, the pediatric patient is about 1 year of age or less.

Another embodiment is a dosing regimen for treating hepatoblastoma in a pediatric patient comprising: (a) administering a dose of about 1 mg/kg to about 5 mg/kg or about 10 mg/m$^2$ to about 300 mg/m$^2$ per cycle of cisplatin; (b) administering about 5 g/m$^2$ to about 25 g/m$^2$ of sodium thiosulfate per cycle of the cisplatin, wherein the sodium thiosulfate is administered from about 2 hours to about 6 hours after the administration of the cisplatin; and wherein the dosing regimen achieves a reduction in ototoxicity when dosed to a pediatric patient compared to a dosing regimen not including the sodium thiosulfate, which is dosed to a pediatric patient, wherein ototoxicity is determined by one or more criteria selected from: (a) a reduction in hearing measured by a 20 dB loss at a single frequency; (b) a reduction in hearing measured by a 10 dB loss at two consecutive frequencies; (c) loss of response at three consecutive test frequencies where responses were previously obtained; (d) a reduction in bilateral high-frequency hearing characterized by the criteria: (i) a <40 dB hearing loss at all frequencies, which indicates a grade 0 or minimal hearing loss; (ii) a ≥40 dB hearing loss at 8,000 Hz only, which indicates a grade 1 or mild hearing loss; (iii) a ≥40 dB hearing loss at 4,000 Hz and above, which indicates a grade 2 or moderate hearing loss; (iv) a ≥40 dB hearing loss at 2,000 Hz and above, which indicates a grade 3 or marked hearing loss; (v) a ≥40 dB hearing loss at 1,000 Hz and above, which indicates a grade 4 or severe hearing loss; or (e) a reduction in hearing characterized by the criteria: (i) a ≤20 dB hearing loss at all frequencies, which indicates a grade 0 hearing loss; (ii) a >20 dB HL above 4,000 Hz, which indicates a grade 1 hearing loss; (iii) a >20 dB HL at 4,000 Hz and above, which indicates a grade 2 hearing loss; (iv) a >20 dB HL at 2,000 Hz or 3,000 Hz, which indicates a grade 3 hearing loss; (v) a >40 dB HL at 2,000 Hz and above, which indicates a grade 1 hearing loss; wherein a change in hearing is computed relative to baseline measures prior to the patient receiving a platinum based chemotherapeutic or sodium thiosulfate or both. In one aspect, the regimen comprises administering a sodium thiosulfate pharmaceutical composition as described herein. In another aspect, the pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

Another embodiment is method of reducing ototoxicity in a pediatric patient of about 12 years of age and under having a standard risk or an intermediate risk hepatoblastoma and receiving a dose of about 1 mg/kg to about 5 mg/kg or about 10 mg/m$^2$ to about 300 mg/m$^2$ per cycle of cisplatin, the method comprising administering about 5 g/m$^2$ to about 25 g/m$^2$ of sodium thiosulfate per cycle of the cisplatin about six hours after the administration of the cisplatin, wherein ototoxicity is determined by one or more criteria selected from: (a) a reduction in hearing measured by a 20 dB loss at a single frequency; (b) a reduction in hearing measured by a 10 dB loss at two consecutive frequencies; (c) loss of response at three consecutive test frequencies where responses were previously obtained; (d) a reduction in bilateral high-frequency hearing characterized by the criteria: (i) a <40 dB hearing loss at all frequencies, which indicates a grade 0 or minimal hearing loss; (ii) a ≥40 dB hearing loss at 8,000 Hz only, which indicates a grade 1 or mild hearing loss; (iii) a ≥40 dB hearing loss at 4,000 Hz and above, which indicates a grade 2 or moderate hearing loss; (iv) a ≥40 dB hearing loss at 2,000 Hz and above, which indicates a grade 3 or marked hearing loss; (v) a ≥40 dB hearing loss at 1,000 Hz and above, which indicates a grade 4 or severe hearing loss; or (e) a reduction in hearing characterized by the criteria: (i) a ≤20 dB hearing loss at all frequencies, which indicates a grade 0 hearing loss; (ii) a >20 dB HL above 4,000 Hz, which indicates a grade 1 hearing loss; (iii) a >20 dB HL at 4,000 Hz and above, which indicates a grade 2 hearing loss; (iv) a >20 dB HL at 2,000 Hz or 3,000 Hz, which indicates a grade 3 hearing loss; (v) a >40 dB HL at 2,000 Hz and above, which indicates a grade 1 hearing loss; wherein a change in hearing is computed relative to baseline measures prior to the patient receiving a platinum based chemotherapeutic or sodium thiosulfate or both; and wherein the administration of sodium thiosulfate does not substantively affect relapse free survival or overall survival compared to a pediatric patient not administered sodium thiosulfate; and wherein the administration of sodium thiosulfate does not lead to substantively increased incidence of one or more adverse events comprising febrile neutropenia, infection, hypomagnesemia, hypernatremia, vomiting, or nausea. In one aspect, the method comprises administering a sodium thiosulfate pharmaceutical composition as described herein. In another aspect, the pharmaceutical composition comprises about 0.5 M of aqueous anhydrous sodium thiosulfate, about 0.01 M of sodium phosphate, pH 6.5, and water. In another aspect, the formulation comprises about 0.5 M of aqueous anhydrous sodium thiosulfate, about 0.004 M of boric acid, pH 8.6-8.8, and water. In another aspect, the formulation comprises about 0.5 M of aqueous anhydrous sodium thiosulfate, about 0.01 M to about 0.05 M of glycine, pH 8.5-8.9, and water. In another aspect, the formulation comprises about 0.5 M of aqueous anhydrous sodium thiosulfate, about 0.01 M to about 0.05 M of tris(hydroxymethyl)aminomethane (tromethamine), pH 8.5-8.9, and water.

One or more embodiments or aspects may be incorporated in a different embodiment or aspect although not specifically described. That is, all embodiments and aspects can be combined in any way or combination.

DETAILED DESCRIPTION

Figure 1:
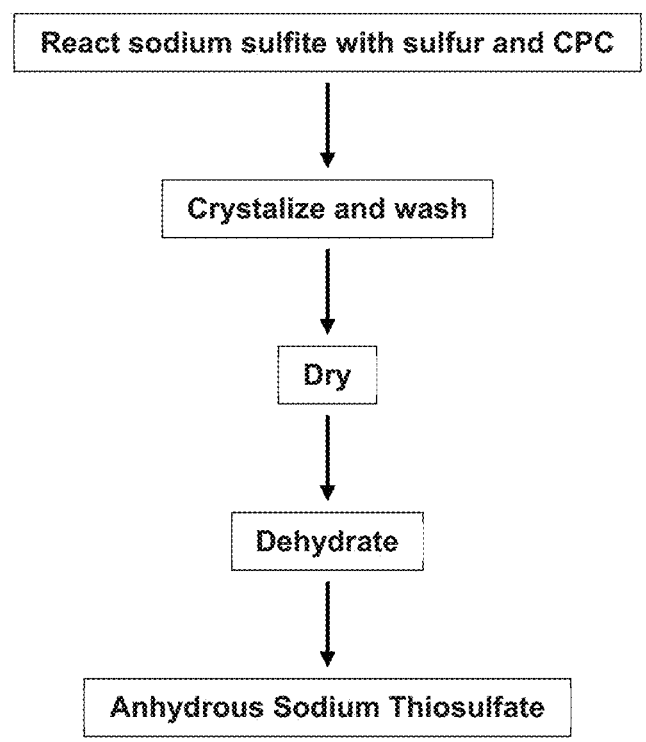
FIG. 1 shows a scheme for synthesizing anhydrous sodium thiosulfate.

The terms "active ingredient", "active pharmaceutical ingredient," or "API" as used herein refer to a pharmaceutical agent, active ingredient, compound, or substance, compositions, or mixtures thereof, that provide a pharmacological, often beneficial, effect.

The term "dose" as used herein denotes any form of the active ingredient formulation that contains an amount sufficient to produce a therapeutic effect with a single administration.

The term "dosage" as used herein refers to the administering of a specific amount, number, and frequency of doses over a specified period of time, typically 1 day.

The terms "active pharmaceutical ingredient load" or "drug load" as used herein refers to the quantity (mass) of the active pharmaceutical ingredient comprised in a single soft capsule fill.

The terms "formulation" or "pharmaceutical composition" as used herein refers to the drug in combination with pharmaceutically acceptable excipients.

The term mean "particle size distribution" (PSD) as used herein refers to the mean particle size from a statistical distribution of a range of particle sizes as described herein. The distribution may be a Gaussian, normal distribution, or a non-normal distribution.

The terms such as "d90," "d50," and "d10" refer to the percentage (e.g., 90%, 50%, or 10%, respectively) of particle sizes that are less than a specified size, range, or distribution. For example, "d90≤100 μm" as means that 90% of the particle sizes within a distribution of particles are less than or equal to 100 μm.

As used herein, the term "patient" refers to any subject including mammals and humans. The patient may have a disease or suspected of having a disease and as such is being treated with a drug. In some instances, the patient is a mammal, such as a human, non-human primate, dog, cat, horse, cow, goat, pig, rabbit, rat, mouse, or a premature neonate, neonate, infant, juvenile, adolescent, or adult thereof. In some instances, the term "patient," as used herein, refers to a human (e.g., a man, a woman, or a child). In some instances, the term "patient," as used herein, refers to laboratory animal of an animal model study. The patient or subject may be of any age, sex, or combination thereof. In some embodiments described herein, the patient is treated with a platinum based chemotherapeutic, such as cisplatin, followed by administration of sodium thiosulfate or a formulation thereof.

The term "pediatric patient" refers to a pediatric mammal or human. In some instances, the patient is a mammal, such as a human, non-human primate, dog, cat, horse, cow, goat, pig, rabbit, rat, mouse, or a premature neonate, neonate, infant, toddler, child, adolescent, juvenile, or teenager thereof. The pediatric patient may be of any ethnicity or sex. The pediatric patient may be of any age, which would be understood to the person of skill in the art to be a pediatric patient in medicine and in veterinary medicine. For example, a human pediatric patient may be a neonate up to 18 years of age. A newborn pediatric is understood to be birth to 1 month of age; an infant is 1 month to 2 years of age; a child is 2 years to 12 years of age; and an adolescent is 12 to 18 years of age. In some countries, a pediatric patient includes those up to the age of 21 years of age. The pediatric patient may have a disease or suspected of having a disease and as such is being treated with a drug. In some embodiments as described further herein, the pediatric patient is treated with a platinum based chemotherapeutic such as cisplatin.

The term "ototoxicity" refers to any type of toxicity that affects the ear. The toxicity may be to the cochlea (e.g., cochleotoxicity), cochlear hair cells, the auditory nerve, or the vestibular system or any of these systems found in the ear or any of these systems in combination. The toxicity can manifest as hearing loss, sensorineural hearing loss, dysequilibrium, tinnitus, or hearing sensitivity or combinations thereof. When referring to hearing loss, the amount of toxicity causing the hearing loss can be mild, moderate, severe, profound, or total resulting in complete deafness. Alternatively, the hearing loss may present at specific frequencies including both high and low frequencies and all iterations of frequencies normal to mammalian hearing. The toxicity can be unilateral, bilateral, bilateral symmetric, or bilateral asymmetric with one ear being affected more than the other is.

The terms "biological sample" or "sample" as used herein refers to a sample obtained or derived from a patient. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), urine, fluids of the eye (e.g., vitreous fluid, aqueous humor), lymph fluid, lymph node tissue, spleen tissue, bone marrow, and fluid from the auditory cavity.

The term "treating" refers to administering a therapy in an amount, manner, or mode effective (e.g., a therapeutic effect) to improve a condition, symptom, disorder, or parameter associated with a disorder, or a likelihood thereof.

The term "prophylaxis" refers to preventing or reducing the progression of a disorder, either to a statistically significant degree or to a degree detectable to one skilled in the art.

The terms "essentially" or "substantially" as used herein mean to a great or significant extent, but not completely.

The term "about" as used herein refers to any values, including both integers and fractional components that are within a variation of up to ±10% of the value modified by the term "about."

As described herein, it was found that sodium thiosulfate (STS) reduces ototoxicity in pediatric patients being treated with platinum based chemotherapeutics. It was surprisingly found that children under the age of 12 have higher rates of ototoxicity and children under the age of 5 are even more at risk. It was further found that the administration of STS after a platinum based chemotherapeutic (e.g., cisplatin) significantly reduced ototoxicity in these pediatric patients. In particular, it was discovered that STS could reduce the severity of ototoxicity, such as Brock grade 2 and 3 ototoxicities. Further, it was identified that the total amount of cisplatin exposure or cumulative dose did not interfere with STS mediated otoprotection. In addition, it was discovered that STS is highly suitable as an otoprotective drug when used in conjunction with local (non-disseminated) cancers. Reference is made to International Patent Application Publication No. WO 2019/108592, which is a continuation of U.S. patent application Ser. No. 15/826,243, filed on Nov. 29, 2017, both of which are incorporated by reference herein in their entirety.

Sodium thiosulfate (also known as sodium hyposulfite) is a water-soluble thiol compound with the formula $Na_2S_2O_3$. The compound is available as anhydrous and crystalline forms; the pentahydrate crystalline form is the most common hydrate form. STS is commercially available as an established antidote for acute cyanide poisoning. STS is a reducing agent and has been used in oncology for preventing cisplatin nephrotoxicity, carboplatin ototoxicity, and as an antidote for extravasation of various chemotherapy agents. The mechanism by which sodium thiosulfate reduces the nephrotoxicity caused by cisplatin and the ototoxicity by carboplatin is not understood. Proposed mechanisms of action involve its thiol group, which allow it to act as a free radical scavenger and/or by covalent binding and inactivating the platinum compound. Sodium thiosulfate reacts irreversibly with cisplatin to form $Pt(S_2O_3)_4$ when the drugs are given simultaneously, successively, or nearly contemporaneously. It is also believed that sodium thiosulfate protects against nephrotoxicity by reducing delivery of cisplatin to the kidneys and by neutralizing cisplatin in the kidneys where sodium thiosulfate is highly concentrated. Following IV administration, sodium thiosulfate is distributed throughout the extracellular fluid. Some sodium thiosulfate is converted to sulfate in the liver. Up to 95% is excreted in the urine unmodified. The biological half-life is 0.65 hours (range: dependent on dose 16.5-182 minutes). When given intravenously, STS is rapidly excreted by the kidney.

While not being bound by any theory, it is believed that the biological effects of STS in preventing cisplatin-induced ototoxicity include binding to the electrophilic platinum molecules, the scavenging of reactive oxygen species, and the increased concentration in cochlear endolymph. Thus, a single effective dosage scavenges any residual platinum chemotherapeutic so that it cannot accumulate and damage the cochlear hair. The results from two phase III clinical trials demonstrated that the efficacy of cisplatin based chemotherapeutics in pediatric patients was not affected when STS was administered.

In addition, STS does not adversely affect the efficacy of several other non-platinum based chemotherapeutics such as doxorubicin and etoposide. In vitro studies of small cell lung cancer cell cultures showed no reduction of cytotoxicity for etoposide after the immediate or delayed addition of STS followed by incubation for 72 hours. Similar studies showed no reduction of anti-tumor activity by STS for doxorubicin, carmustine (BCNU), paclitaxel, or methotrexate. Owing to its ability to scavenge free platinum containing compounds, STS was extensively tested in the clinic, as further described herein, and found to be a highly effective otoprotective compound for pediatric patients.

One embodiment described herein is sodium thiosulfate. Another embodiment described herein is anhydrous sodium thiosulfate. In another embodiment, the sodium thiosulfate does not comprise a hydrate. In another embodiment, the sodium thiosulfate does not comprises sodium thiosulfate pentahydrate. In one embodiment, the sodium thiosulfate comprises crystalline anhydrous sodium thiosulfate. In one embodiment, the sodium thiosulfate comprises amorphous anhydrous sodium thiosulfate. In another embodiment, the sodium thiosulfate comprises aqueous anhydrous sodium thiosulfate.

One embodiment is anhydrous sodium thiosulfate synthesized as described herein.

Another embodiment described herein is a method for synthesizing anhydrous sodium thiosulfate. In one aspect, sodium thiosulfate is synthesized by reacting aqueous sodium sulfite with sulfur in the presence of a detergent, such as cetylpyridinium chloride (CPC). In one embodiment, about 1.0 mole equivalent of sodium sulfite is reacted with 1.1 mole equivalent of sulfur and 0.00013 mole equivalents of cetylpyridinium chloride. In one aspect, the reaction is conducted at elevated temperature. In another aspect, the reaction is conducted at about 75° C. to about 100° C. for a period of about 5 min to 5 hours. In another aspect, the reaction is conducted at about 90° C. for about 5 min to 3 hours. In one aspect, the reaction is heated to about 90° C. and the reaction is completed upon reaching about 90° C. In another aspect, the reaction is cooled following the reaction. In one aspect, the reaction is cooled to room temperature. In another aspect, the reaction is cooled to <2° C. In another aspect, the sodium thiosulfate is washed using a washing solvent. In another aspect, the sodium thiosulfate is washed using acetone. In another aspect, the sodium thiosulfate is washed multiple times. In another aspect, the sodium thiosulfate is washed one time. In another aspect, the sodium thiosulfate is dehydrated by heating and/or filtering. In another aspect, the sodium thiosulfate is dehydrated using a dehydrating solvent. In one aspect, the dehydrating solvent is an alcohol. In another aspect, the dehydrating solvent is methanol. In another aspect, the dehydrating solvent is methanol that has been heated to between 30° C. and 80° C. In another aspect, the sodium thiosulfate is dehydrated multiple times. In another aspect, the sodium thiosulfate is dehydrated one time.

In one embodiment, the anhydrous sodium thiosulfate is milled or micronized to a defined particle size. In one embodiment, the anhydrous sodium thiosulfate comprises a particle size range of about 1 µm to about 500 µm, including all integers and fractions within the specified range. In one aspect, the micronized anhydrous sodium thiosulfate particles have a particle size of about 1 µm to about 100 µm. In one aspect, the micronized anhydrous sodium thiosulfate particles have a particle size of about 5 µm to about 50 µm. In another aspect, the solid particles of anhydrous sodium thiosulfate comprise a distribution of particle sizes, comprising particles of any of the foregoing particle sizes.

In another embodiment, the anhydrous sodium thiosulfate particles have mean particle size distributions (PSD) ranging from about 5 µm to about 300 µm, including all integers and fractions within the specified range. In one aspect, the solid particles of anhydrous sodium thiosulfate comprise mean particle size distributions of about 5 µm, about 10 µm, about 15 µm, about 20 µm, 25 µm, about 30 µm, about 40 µm, about 50 µm, about 60 µm, about 70 µm, about 80 µm, about 90 µm, about 100 µm, about 120 µm, about 140 µm, about 160 µm, about 180 µm, about 190 µm, about 200 µm, about 220 µm, about 240 µm, about 260 µm, about 280 µm, or about 300 µm.

In one embodiment, the solid particles of anhydrous sodium thiosulfate have a mean particle size distribution d50 of about 5 µm to about 100 µm. In one embodiment, the solid particles of anhydrous sodium thiosulfate have a mean particle size distribution d50 of about 5 µm to about 50 µm. In one aspect, the solid particles of anhydrous sodium thiosulfate have a mean particle size distribution d50 of about 10 µm to about 25 µm.

In another embodiment, the anhydrous sodium thiosulfate particles have a particle size distribution with a d90 of less than or equal to about 100 µm. In one aspect, the particle size distribution of solid particles of anhydrous sodium thiosulfate have a d90 of ≤ to about 50 µm. In one aspect, the solid particles of anhydrous sodium thiosulfate have a particle size distribution with a d90 of ≤ about 25 µm (d90≤25 µm).

In another embodiment, the solid particles of anhydrous sodium thiosulfate comprise multiple distributions of particle sizes. In one aspect, the solid particles of anhydrous sodium thiosulfate may comprise a plurality of independently combined mean particle size distributions, wherein each independent mean particle size distribution ranges from about 5 µm to about 100 µm, including all integers and fractions within the specified range. In another aspect, the solid particles of anhydrous sodium thiosulfate may comprise a plurality of independently combined mean particle size distributions, wherein each independent mean particle size distribution ranges from about 5 µm to about 50 µm, including all integers and fractions within the specified range. In another aspect, the solid particles of anhydrous sodium thiosulfate comprise a combination of independently combined mean particle size distributions of about 10 µm to about 30 µm including all integers and fractions within the specified range. Any of the foregoing particle size distributions may be combined to provide the desired size distribution range.

The foregoing sizes of anhydrous sodium thiosulfate particles may be determined using standard techniques known to one of ordinary skill in the art. The exemplary techniques that can be used for measuring the size of anhydrous sodium thiosulfate particles may include laser diffraction analysis, light scattering (e.g., dynamic light scattering), microscopic particle image analysis, elutriation, or aerosol mass spectrometry. The sample of anhydrous sodium thiosulfate particles may be measured as a dry sample or a wet sample. Any commercially available instrument for measuring particle sizes may be used, including instruments from Cilas; Brookhaven Instruments Corporation; Malvern Instruments; Horiba Scientific; or Wyatt following the recommended operating procedures according to the manufacturer's instructions.

The measured particle sizes using the techniques described herein may be expressed as a derived diameter with a normal distribution or non-normal distribution with a mean, median (e.g., mass median diameter), and mode of particle diameter sizes. The particle size distribution may be expressed as a diameter number distribution, a surface area distribution, or a particle volume distribution. The mean of the particle size distribution may be calculated and expressed in various ways, such as the volume mean diameter (D[4,3] or $d_{43}$), mean surface area diameter (D[3,2] or $d_{32}$) or the mean number particle diameter (D[1,0] or $d_{10}$). Because the particle size distribution values vary depending on the measurement methodology and how the distribution is expressed, the comparison of different mean particle size distributions must be calculated by the same methodology in order to yield an accurate comparison. For example, a sample with a measured and calculated volume mean diameter must be compared with a second sample having a measured and calculated volume mean diameter, ideally measured using the same measuring instrument under the same conditions. Thus, the specific particle size distributions described herein are not intended to be limited to any one type of method for measuring or calculating a particle size distribution (e.g., a diameter number distribution, a surface area distribution, or a particle volume distribution), but rather indicate particle size values and distributions thereof for each method of measuring particle sizes described herein.

Another embodiment described herein is anhydrous sodium thiosulfate made by the methods described herein. Another embodiment is a means for preparing anhydrous sodium thiosulfate.

Another embodiment described herein is anhydrous sodium thiosulfate characterized by an X-ray powder diffraction (XRPD) pattern comprising at least four peaks at 10.52, 15.13, 17.71, 19.70, 21.09, 21.49, 21.84, 27.40, 28.96, 30.46, 31.81, 32.52, 33.15, 37.40, or 38.16 degrees 2 theta (2 θ)±0.2, when the XRPD is collected from about 2 to about 40 degrees 2 θ using copper Kα radiation. In one embodiment, the anhydrous sodium thiosulfate characterized by an X-ray powder diffraction (XRPD) pattern comprising at least four peaks selected from 10.52, 15.13, 19.70, 21.49, 21.84, 28.96, 30.46, 33.15, 37.40, or 38.16 degrees 2 theta (2 θ)±0.2, when the XRPD is collected from about 2 to about 40 degrees 2 θ using copper Kα radiation. In one embodiment, the anhydrous sodium thiosulfate is characterized by an XRPD pattern substantially similar to the XRPD pattern of FIG. 2A. In another embodiment, the anhydrous sodium thiosulfate is characterized by an X-ray powder diffraction (XRPD) pattern comprising at least 1, at least 2, at least 3, at least 4 at least 5, at least 6 at least 7, at least 8, at least 9, or at least 10 of the peaks shown in Table 5.

Another embodiment described herein is anhydrous sodium thiosulfate comprising: no greater than 0.1 μg/g of cadmium; no greater than 0.25 μg/g lead; no greater than 0.75 μg/g arsenic; no greater than 0.15 μg/g mercury; no greater than 0.25 μg/g cobalt; no greater than 0.5 μg/g vanadium; no greater than 1.0 μg/g nickel; no greater than 12.5 μg/g lithium; no greater than 4.5 μg/g antimony; no greater than 15.0 μg/g copper; no greater than 1500 ppm methanol; no greater than 3% (w/w) water; and no greater than 1.5% (w/w) of total impurities.

Another embodiment described herein is anhydrous sodium thiosulfate comprising essentially no sodium thiosulfate pentahydrate. In one aspect, anhydrous sodium thiosulfate comprises less than 1%, less than 0.5%, less than 0.2%, less than 0.1%, less than 0.05%, or less than 0.001% sodium thiosulfate pentahydrate.

Another embodiment described herein is an assay for measuring the concentration of cisplatin. In one aspect, the assay comprises measuring the cisplatin concentration using HPLC and UV detection and comparing the retention time and peak area to a standard curve of cisplatin concentration assayed under similar conditions. Another embodiment described herein is a means for determining a cisplatin concentration as described herein.

Another embodiment described herein is an assay for determining the cisplatin binding capacity of a composition of sodium thiosulfate. The sodium thiosulfate composition may be sodium thiosulfate pentahydrate, anhydrous sodium thiosulfate, aqueous anhydrous sodium thiosulfate, or a pharmaceutical composition of sodium thiosulfate. The assay comprises combining various concentrations of sodium thiosulfate with a concentration of cisplatin and then measuring the apparent diminution of cisplatin concentration using HPLC and UV detection over a time course. In one aspect, the mole ratio of sodium thiosulfate to cisplatin is 10:1, 7:1, 6:1, 5:1, 3:1, 2:1, or 1:1. In one aspect, the mole ratio of sodium thiosulfate to cisplatin is 10:1, 6:1, or 5:1. In one aspect, the apparent diminution of cisplatin concentration owing to binding by sodium thiosulfate is linear over time. In another aspect, the cisplatin concentration is measured about 5 mins after mixing with sodium thiosulfate and is measured every 10, 20, 30, or 60 min for a period of 0.5, 1, 2, 3, 4, 5, or 6 hours. In one aspect, the cisplatin concentration is determined about 5 mins after mixing with sodium thiosulfate and is measured every 30 min for a period of 2 hours. In one aspect, a mixed mode C-18 chromatography column is used in the assay, which has both hydrophobic interaction and ion exchange capabilities. In another aspect, the HPLC run time for the assay is about 2 min, about 5 min, about 7.5 min, about 10 min or about 15 min. In one aspect, the HPLC run time is about 5 min or about 10 min. In another aspect, cisplatin elutes from the HPLC under the assay conditions after about 1.5 min to about 2.5 min. In one aspect, cisplatin elutes from the HPLC under the assay conditions after about 2 min. In another aspect, sodium thiosulfate elutes from the HPLC under the assay conditions after about 5 min to about 7.0 min. In one aspect, cisplatin elutes from the HPLC under the assay conditions after about 6 min.

Another embodiment described herein is a means for determining a sodium thiosulfate binding capacity for cisplatin as described herein.

Without being bound by any theory, factors that affect cisplatin binding by sodium thiosulfate in the assay described herein include the temperature, relative concentration of sodium thiosulfate, and the time elapsed between mixing cisplatin with sodium thiosulfate and HPLC measurement. An HPLC autosampler allows tight temperature control and facilitates sample preparation and analysis. In addition, this method provides the change in concentration of cisplatin over time as opposed to at a single time point. This method can be used to determine a reaction rate under given conditions or a half-life for comparisons between different samples of sodium thiosulfate.

Another embodiment described herein is an assay for measuring the binding capacity of sodium thiosulfate for cisplatin based on the apparent diminution of cisplatin concentration after combining various mole ratios of cisplatin and sodium thiosulfate, the method comprising: mixing various mole ratios of sodium thiosulfate with predetermined quantities of cisplatin; incubating the mixture for a period of time; and analyzing the concentration of cisplatin. In one aspect, the mole ratio of sodium thiosulfate to cisplatin is 10:1 to 1:1. In one aspect, the mole ratio of sodium thiosulfate to cisplatin is 10:1, 7:1, 6:1, 5:1, 3:1, 2:1, or 1:1. In one aspect, the mixture is incubated at about 25° C. for about 5 min, about 35 min, about 65 min, about 95 min, and about 125 min and analyzed. In another aspect, the concentration is analyzed using HPLC with a mixed mode C-18 chromatography column at a column temperature of 35° C., flow rate of 400 μL/min, and UV detection at 220 nm. In one aspect, the HPLC method comprises a step gradient of 100% Buffer A (0.5 mM ammonium formate in 9:1 water:acetonitrile, pH 4) for 3 min; then 90% Buffer A and 10% Buffer B (200 mM ammonium formate in 7:3 water:acetonitrile, pH 4) for 3.5 min; then 100% Buffer A for 4.5 min.

Another embodiment described herein is a pharmaceutical composition or formulation comprising sodium thiosulfate. In one aspect, the sodium thiosulfate comprises anhydrous sodium thiosulfate. The formulation is suitable for administration through any conventional route including intravenously, subcutaneously, intramuscularly, intraperitoneally, intrathecally, orally, rectally, vaginally, or a combination thereof. In one aspect, the formulation is administered intravenously.

In one embodiment, the pharmaceutical compositions described herein provide a composition of sodium thiosulfate for administration to a subject. The sodium thiosulfate can be administered, for example, to a subject, or a subject in need thereof.

Another embodiment described herein is a pharmaceutical composition comprising sodium thiosulfate. In one aspect, the composition comprises sodium thiosulfate and one or more pharmaceutically acceptable excipients. In another aspect, the composition comprises sodium thiosulfate and a buffer. In another aspect, the composition comprises anhydrous sodium thiosulfate and a buffer. In one aspect, the composition comprises a liquid formulation of anhydrous sodium thiosulfate and a buffer. In another aspect, the composition is a dry or lyophilized composition comprising sodium thiosulfate and one or more buffers that is reconstituted with sterile water for injection prior to administration. In another aspect, the composition comprises aqueous anhydrous sodium thiosulfate, one or more buffers, and a solvent. As used herein, "aqueous anhydrous sodium thiosulfate" refers to anhydrous sodium thiosulfate that has been solubilized in an aqueous solvent. In another aspect, the composition comprises aqueous anhydrous sodium thiosulfate, one or more buffers, one or more agents to adjust the pH, and a solvent. In another aspect, the composition comprises aqueous anhydrous sodium thiosulfate, one or more buffers, one or more agents to adjust the pH, a solvent, and one or more preservatives, physiological salts, carriers, or pharmaceutically acceptable excipients. In one embodiment, the pharmaceutical formulation comprises that shown in Table 1.

TABLE 1

Exemplary Sodium Thiosulfate Formulation

| Ingredient | Concentration/Amount |
|---|---|
| Sodium thiosulfate | 0.1-2M |
| Buffer(s) | 0.001-0.5M |
| pH adjusting agent(s): e.g., NaOH, HCl | As needed to adjust to pH 5-8 |
| Preservatives, physiological salts, carriers, pharmaceutically acceptable excipients | Optional; up to 25% by mass |
| Solvent (e.g., sterile water for injection) | quantum sufficit (q.s.) |

In another embodiment, the formulation comprises aqueous anhydrous sodium thiosulfate and water. In another aspect, the formulation comprises aqueous anhydrous sodium thiosulfate, water, a buffer, and one or more pH-adjusting agents. In another aspect, the formulation comprises aqueous anhydrous sodium thiosulfate, water, phosphate buffer, and one or more pH-adjusting agents to bring the pH to about 6.5. In another aspect, the formulation comprises aqueous anhydrous sodium thiosulfate, water, borate buffer, and one or more pH-adjusting agents to bring the pH to about 8.5-8.8. In another aspect, the formulation comprises aqueous anhydrous sodium thiosulfate, water, glycine, and one or more pH-adjusting agents to bring the pH to about 8.5-8.9. In another aspect, the formulation comprises aqueous anhydrous sodium thiosulfate, water, tris(hydroxymethyl)aminomethane (tromethamine) buffer, and one or more pH-adjusting agents to bring the pH to about 8.5-8.9. In one embodiment, the pharmaceutical formulation comprises one of the formulations shown in Table 2. The following formulations are exemplary and the identity and concentration of the buffers can be adjusted over the range of about 0.001 M to about 0.5 M and the mg/mL and percent weight adjusted accordingly.

TABLE 2

Exemplary Sodium Thiosulfate Formulations (solution)

| Component | Mass/Volume | Molarity | Percent Weight |
|---|---|---|---|
| Sodium thiosulfate, anhydrous | 80.0 mg/mL | 0.5M | 8% |
| Sodium phosphate, pH 6.5 | 1.4 mg/mL | 0.01M | 0.12% |
| Sodium thiosulfate, anhydrous | 80.0 mg/mL | 0.5M | 8% |
| Boric acid, pH 8.6-8.8 | 0.25 mg/mL | 0.004M | 0.023% |
| Sodium thiosulfate, anhydrous | 80.0 mg/mL | 0.5M | 8% |
| Glycine, pH 8.5-8.9 | 0.75 mg/mL | 0.01M | 0.069% |
| Sodium thiosulfate, anhydrous | 80.0 mg/mL | 0.5M | 8% |
| Tris(hydroxymethyl)aminomethane (tromethamine), pH 8.5-8.9 | 1.21 mg/mL | 0.01M | 0.11% |

In one embodiment, the formulation comprises about 0.1 M; about 0.2 M; about 0.3 M; about 0.4 M; about 0.5 M; about 0.6 M; about 0.7 M; about 0.8 M; about 0.9 M; about 1.0 M; about 1.1 M; about 1.2 M; about 1.3 M; about 1.4 M; about 1.5 M; about 1.6 M; about 1.7 M; about 1.8 M; about 1.9 M; or about 2.0 M of aqueous anhydrous sodium thiosulfate.

In another embodiment, the formulation comprises about 0.1 M to about 2.0 M; about 0.1 M to about 0.5 M; about 0.1 M to about 0.6 M; about 0.1 M to about 0.7 M; about 0.1 M to about 0.8 M; about 0.1 M to about 1.0 M; about 0.2 M to about 0.5 M; about 0.2 M to about 0.6 M; about 0.2 M to about 0.7 M; about 0.2 M to about 0.8 M; about 0.2 M to about 1.0 M; about 0.3 M to about 0.5 M; about 0.3 M to about 0.6 M; about 0.3 M to about 0.7 M; about 0.3 M to about 0.8 M; about 0.3 M to about 1.0 M; about 0.4 M to about 0.5 M; about 0.4 M to about 0.6 M; about 0.4 M to about 0.7 M; about 0.4 M to about 0.8 M; about 0.4 M to about 1.0 M; about 0.5 M to about 0.6 M; about 0.5 M to about 0.7 M; about 0.5 M to about 0.8 M; about 0.5 M to about 1.0 M; about 0.6 M to about 0.7 M; about 0.6 M to about 0.8 M; or about 0.6 M to about 1.0 M of aqueous anhydrous sodium thiosulfate.

In another embodiment, the formulation comprises about 20 mg/mL; about 40 mg/mL; about 60 mg/mL; about 80 mg/mL; about 100 mg/mL; about 120 mg/mL; about 140 mg/mL; about 160 mg/mL; about 180 mg/mL; about 200 mg/mL; about 220 mg/mL; about 240 mg/mL; about 260 mg/mL; about 280 mg/mL; about 300 mg/mL; or about 320 mg/mL of aqueous anhydrous sodium thiosulfate.

In another embodiment, the formulation comprises about 10 mg/mL to about 320 mg/mL; about 10 mg/mL to about 80 mg/mL; about 10 mg/mL to about 100 mg/mL; about 10 mg/mL to about 110 mg/mL; about 10 mg/mL to about 120 mg/mL; about 10 mg/mL to about 160 mg/mL; about 20 mg/mL to about 80 mg/mL; about 20 mg/mL to about 100 mg/mL; about 20 mg/mL to about 110 mg/mL; about 20 mg/mL to about 120 mg/mL; about 20 mg/mL to about 160 mg/mL; about 30 mg/mL to about 80 mg/mL; about 30 mg/mL to about 100 mg/mL; about 30 mg/mL to about 110 mg/mL; about 30 mg/mL to about 120 mg/mL; about 30 mg/mL to about 160 mg/mL; about 40 mg/mL to about 80 mg/mL; about 40 mg/mL to about 100 mg/mL; about 40 mg/mL to about 110 mg/mL; about 40 mg/mL to about 120 mg/mL; about 40 mg/mL to about 160 mg/mL; about 60 mg/mL to about 80 mg/mL; about 60 mg/mL to about 100 mg/mL; about 60 mg/mL to about 110 mg/mL; about 60 mg/mL to about 120 mg/mL; about 60 mg/mL to about 160 mg/mL; about 80 mg/mL to about 100 mg/mL; about 80 mg/mL to about 110 mg/mL; about 80 mg/mL to about 120 mg/mL; about 80 mg/mL to about 160 mg/mL; about 100 mg/mL to about 110 mg/mL; about 100 mg/mL to about 120 mg/mL; or about 100 mg/mL to about 160 mg/mL of aqueous anhydrous sodium thiosulfate.

In another embodiment, the formulation comprises about 1%; about 2%; about 4%; about 6%; about 8%; about 10%; about 12%; about 14%; about 16%; about 18%; about 20%; about 22%; about 24%; about 26%; about 28%; about 30%; or about 32% by mass of aqueous anhydrous sodium thiosulfate.

In another embodiment, the formulation comprises about 1% to about 32%; about 1% to about 8%; about 1% to about 10%; about 1% to about 11%; about 1% to about 12%; about 1% to about 16%; about 2% to about 8%; about 2% to about 10%; about 2% to about 11%; about 2% to about 12%; about 2% to about 16%; about 3% to about 8%; about 3% to about 10%; about 3% to about 11%; about 3% to about 12%; about 3% to about 16%; about 4% to about 8%; about 4% to about 10%; about 4% to about 11%; about 4% to about 12%; about 4% to about 16%; about 6% to about 8%; about 6% to about 10%; about 6% to about 11%; about 6% to about 12%; about 6% to about 16%; about 8% to about 10%; about 8% to about 11%; about 8% to about 12%; about 8% to about 16%; about 10% to about 11%; about 10% to about 12%; or about 10% to about 16% by mass of aqueous anhydrous sodium thiosulfate.

In one embodiment described herein, the formulation comprises one or more buffers. Typical buffers are pharmaceutically acceptable buffers. In one aspect the one or more buffer comprises acetic acid, acetylsalicylic acid, adipic acid, alginic acid, ascorbic acid, aspartic acid, benzoic acid, benzenesulfonic acid, bisulfic acid, boric acid, butanoic acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, gly-glycine, gluco heptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthalenesulfonic acid, naphthilic acid, nicotinic acid, nitrous acid, oxalic acid, pelargonic, phosphoric acid, propionic acid, pyruvic acid, saccharin, salicylic acid, sorbic acid, succinic acid, sulfuric acid, tartaric acid, thiocyanic acid, thioglycolic acid, thiosulfuric acid, tosylic acid, undecylenic acid, MES, bis-tris methane, ADA, ACES, bis-tris propane, PIPES, MOPSO, cholamine chloride, MOPS, BES, TES, HEPES, DIPSO, MOBS, acetamido glycine, TAPSO, TEA, POPSO, HEPPSO, EPS, HEPPS, Tricine, Tris(hydroxymethyl)aminomethane (tromethamine), glycinamide, glycylglycine, HEPBS, Bicine, TAPS, AMPB, CHES, AMP, AMPSO, CAPSO, CAPS, CABS, combinations thereof, or salts thereof. In one aspect, the buffer comprises one or more of phosphate, sulfate, carbonate, formate, acetate, propionate, butanoate, lactate, glycine, maleate, pyruvate, citrate, aconitate, isocitrate, α-ketoglutarate, succinate, fumarate, malate, oxaloacetate, aspartate, glutamate, tris(hydroxymethyl)aminomethane (tromethamine), combinations thereof, or salts thereof. In one aspect, the buffer is phosphate, glycine, tris(hydroxymethyl)aminomethane (tromethamine), or borate. In one aspect, the buffer is borate. In one aspect, the buffer is phosphate. In one aspect, the buffer is glycine. In one aspect, the buffer is tris(hydroxymethyl)aminomethane (tromethamine).

In another embodiment, the one or more buffers have a concentration of about 0.001 M to about 0.5 M. In one aspect, the one or more buffers have a concentration of about 0.005 M to about 0.2 M; about 0.01 M to about 0.1 M; about 0.005 M to about 0.05 M; about 0.01 M to about 0.05 M; or about 0.005 M to about 0.01 M. In one aspect, the one or more buffers have a concentration of about 0.005 M; about 0.075 M; about 0.01 M; about 0.02 M; about 0.05 M, about 0.1 M; about 0.2 M, or about 0.5 M. In one aspect, the one or more buffers have a concentration of about 0.01 M. In another aspect, the one or more buffers have a concentration of about 0.05 M.

In another embodiment, the formulation comprises one or more buffers that are titrated with one or more pharmaceutically acceptable acids or bases to adjust the pH. In one aspect, the pH of the formulation is about 2 to about 10; about 3 to about 9; about 4 to about 8; about 4 to about 7; about 4 to about 6; about 5 to about 6; about 5 to about 7; about 5 to about 8; about 6.0 to about 6.5; about 6 to about 7; about 6.5 to about 7; or about 6 to about 8. In one aspect the pH of the formulation is about 5.0; about 5.5; about 6.0; about 6.1, about 6.2, about 6.3, about 6.4, about 6.5, about 6.6, about 6.7, about 6.8, about 6.9; about 7.0; or about 7.5. In one aspect, the pH of the formulation is about 6.5.

In another embodiment, the formulation comprises one or more buffers that are titrated with one or more pharmaceutically acceptable acids or bases to adjust the pH to about 6.5. Typically, the acid and base are selected to match the buffer and existing ions in the solution. In one aspect, the pH is raised by the addition of a group IA hydroxide. In one aspect, the hydroxide can be sodium hydroxide or potassium hydroxide. In another aspect, the pH is lowered by the addition of an acid (i.e., a proton donor). Any pharmaceutically acceptable acid can be used. In one aspect, the acid is phosphoric acid. In another aspect, the acid is hydrochloric acid. In one aspect, both sodium hydroxide and hydrochloric acid (or phosphoric acid) are added to the formulation to titrate the pH to about 6.5.

One embodiment described herein is a pharmaceutical formulation as shown in Table 3.

TABLE 3

Exemplary Sodium Thiosulfate Formulations

| Component | Mass/Volume | Molarity |
| --- | --- | --- |
| Sodium thiosulfate, anhydrous | 80.0 mg/mL | 0.5M |
| Sodium phosphate, monobasic, monohydrate | 1.23 mg/mL | 0.0087M |
| Sodium phosphate, dibasic, anhydrous | 0.16 mg/mL | 0.0012M |
| Total phosphate buffer | 1.39 mg/mL | 0.01M |
| Hydrochloric acid or phosphoric acid | q.s. | q.s. |
| Sodium hydroxide | q.s. | q.s. |
| Final pH: 6.0-8.0 | | |

TABLE 3-continued

Exemplary Sodium Thiosulfate Formulations

| Component | Mass/Volume | Molarity |
|---|---|---|
| Sodium thiosulfate, anhydrous | 80.0 mg/mL | 0.5M |
| Boric acid | 0.25 mg/mL | 0.004M |
| Hydrochloric acid | q.s. | q.s. |
| Sodium hydroxide | q.s. | q.s. |
| Final pH: 8.6-8.8 | | |
| Sodium thiosulfate, anhydrous | 80.0 mg/mL | 0.5M |
| Glycine | 0.75 mg/mL | 0.01M |
| Hydrochloric acid | q.s. | q.s. |
| NaOH | q.s. | q.s. |
| Final pH: 8.5-8.9 | | |
| Sodium thiosulfate, anhydrous | 80.0 mg/mL | 0.5M |
| Tris(hydroxymethyl)aminomethane (Tromethane) | 1.21 mg/mL | 0.01M |
| Hydrochloric acid | q.s. | q.s. |
| NaOH | q.s. | q.s. |
| Final pH: 8.5-8.9 | | |

Another embodiment described herein is a pharmaceutical formulation comprising about 0.25 M to about 1.0 M aqueous anhydrous sodium thiosulfate; about 1.0 mM to about 500 mM buffer, pH 5 to 9, and water. In one aspect, the pharmaceutical formulation comprises about 40 mg/mL to about 160 mg/mL aqueous anhydrous sodium thiosulfate; about 1.4 mg/mL phosphate buffer, pH 5 to 8, and water. In another aspect, the pharmaceutical formulation comprises about 4% to about 16% aqueous anhydrous sodium thiosulfate; about 0.14% sodium phosphate buffer pH 5 to 8, and water. In another aspect, the pharmaceutical formulation comprises about 40 mg/mL to about 160 mg/mL aqueous anhydrous sodium thiosulfate; about 0.25 mg/mL borate buffer, pH 6 to 9, and water. In another aspect, the pharmaceutical formulation comprises about 4% to about 16% aqueous anhydrous sodium thiosulfate; about 0.023% borate buffer pH 6 to 9, and water. In another aspect, the pharmaceutical formulation comprises about 40 mg/mL to about 160 mg/mL aqueous anhydrous sodium thiosulfate; about 0.75 mg/mL glycine buffer, pH 6 to 9, and water. In another aspect, the pharmaceutical formulation comprises about 4% to about 16% aqueous anhydrous sodium thiosulfate; about 0.069% glycine buffer pH 6 to 9, and water. In another aspect, the pharmaceutical formulation comprises about 40 mg/mL to about 160 mg/mL aqueous anhydrous sodium thiosulfate; about 1.21 mg/mL tris(hydroxymethyl)aminomethane (tromethamine) buffer, pH 6 to 9, and water. In another aspect, the pharmaceutical formulation comprises about 4% to about 16% aqueous anhydrous sodium thiosulfate; about 0.11% tris(hydroxymethyl)aminomethane (tromethamine) buffer pH 6 to 9, and water.

Another embodiment described herein is a pharmaceutical formulation comprising about 0.5 M aqueous anhydrous sodium thiosulfate, about 0.01 M sodium phosphate, pH 6.5, and water. In one aspect, the pharmaceutical formulation comprises about 80 mg/mL aqueous anhydrous sodium thiosulfate, about 1.4 mg/mL sodium phosphate, pH 6.5, and water. In another aspect, the pharmaceutical formulation comprises about 8% aqueous anhydrous sodium thiosulfate; about 0.14% sodium phosphate, pH 6.5.

Another embodiment described herein is a pharmaceutical formulation comprising about 0.5 M aqueous anhydrous sodium thiosulfate, about 0.004 M boric acid, pH 8.6-8.8, and water. In one aspect, the pharmaceutical formulation comprises about 80 mg/mL aqueous anhydrous sodium thiosulfate, about 0.25 mg/mL boric acid, pH 8.6-8.8, and water. In another aspect, the pharmaceutical formulation comprises about 8% aqueous anhydrous sodium thiosulfate; about 0.023% boric acid, pH 8.6-8.8.

Another embodiment described herein is a pharmaceutical formulation comprising about 0.5 M aqueous anhydrous sodium thiosulfate, about 0.01 M to about 0.05 M glycine, pH 8.5-8.9, and water. In one aspect, the pharmaceutical formulation comprises about 80 mg/mL aqueous anhydrous sodium thiosulfate, about 0.75 mg/mL to about 3.8 mg/mL glycine, pH 8.5-8.9, and water. In another aspect, the pharmaceutical formulation comprises about 8% aqueous anhydrous sodium thiosulfate; about 0.069% to about 0.35% glycine, pH 8.5-8.9.

Another embodiment described herein is a pharmaceutical formulation comprising about 0.5 M aqueous anhydrous sodium thiosulfate, about 0.01 M to about 0.05 M Tris (hydroxymethyl)aminomethane (tromethamine), pH 8.5-8.9, and water. In one aspect, the pharmaceutical formulation comprises about 80 mg/mL aqueous anhydrous sodium thiosulfate, about 1.2 mg/mL to about 3.6 mg/mL Tris (hydroxymethyl)aminomethane (tromethamine), pH 8.5-8.9, and water. In another aspect, the pharmaceutical formulation comprises about 8% aqueous anhydrous sodium thiosulfate; about 0.1% to about 0.33% Tris(hydroxymethyl) aminomethane (tromethamine), pH 8.5-8.9.

Another embodiment described herein is a pharmaceutical composition comprising n aqueous sodium thiosulfate and one or more pharmaceutically acceptable excipients.

Another embodiment described herein is a pharmaceutical composition comprising an aqueous sodium thiosulfate and one or more pharmaceutically acceptable buffers. In one aspect, the pH of the pharmaceutical composition is between 4 and 8. In another aspect, the pH of the pharmaceutical composition is between 5 and 7. In another aspect, the pH of the pharmaceutical composition is between 6 and 7. In another aspect, the pH of the pharmaceutical composition is between 6 and 8. In another aspect, the pH of the pharmaceutical composition is about 6. In another aspect, the pH of the pharmaceutical composition is about 6.5. In another aspect, the pH of the pharmaceutical composition is about 7. In another aspect, the pH of the pharmaceutical composition is about 7.5.

Another embodiment described herein is a pharmaceutical composition comprising aqueous sodium thiosulfate, one or more pharmaceutically acceptable buffers, and one or more salts. In one aspect the one or more salts comprises sodium chloride, potassium chloride, magnesium chloride, calcium chloride, sodium sulfate, potassium sulfate, magnesium sulfate, calcium sulfate, ammonium chloride, ammonium carbonate, ammonium phosphate, ammonium sulfate, potassium citrate, potassium phosphate, potassium lactate, sodium acetate, sodium citrate, sodium lactate, sodium phosphate, among others. In one aspect, the concentration of the one or more salts is from about 0.001 M to about 0.5 M. In another aspect, the concentration of the one or more salts is about 0.001 M, about 0.005 M, about 0.01 M, about 0.05 M, about 0.1 M, about 0.2 M, or about 0.5 M. In one aspect, the concentration of the one or more salts is about 0.05 M to about 0.2 M.

Another embodiment described herein is a pharmaceutical composition comprising an aqueous solution of about 0.2 M to about 2 M of sodium thiosulfate, about 0.001 M to about 0.05 M of a pharmaceutically acceptable buffer, and about 0.005 M to about 0.05 M of a pharmaceutically acceptable salt. In one aspect, the pharmaceutical composition has a pH of about 6 to 8. In one aspect, the pharmaceutical composition comprises about 1 M of sodium thiosulfate, about 0.05 M of a pharmaceutically acceptable buffer, and about 0.05 M of a pharmaceutically acceptable salt, and a pH of about 6 to 8.

Another embodiment described herein is a sodium thiosulfate pharmaceutical composition comprising essentially no borate ions. In one aspect, sodium thiosulfate composition comprises less than 1%, less than 0.5%, less than 0.2%, less than 0.1%, less than 0.05%, or less than 0.001% borate ions. In one aspect, the sodium thiosulfate composition comprises phosphate ions instead of borate ions.

Another embodiment is a method of manufacturing a pharmaceutical sodium thiosulfate formulation. In one embodiment, such composition is made by: (i) combining sodium thiosulfate with a solvent and optionally, one or more pharmaceutically acceptable excipients; (ii) transferring single or multiple doses of the liquid or suspension into suitable containers; and (iii) sealing the containers. In one aspect, the liquid or suspension is filtered and/or sterilized prior to or after transference to suitable containers. In one aspect, the container is an injectable vial or a syringe.

One embodiment is a method for preparing a formulation comprising anhydrous sodium thiosulfate comprising combining anhydrous sodium sulfate with one or more buffers and a solvent. The method further comprises adjusting the pH with pharmaceutically acceptable acids or bases. In one aspect, the buffer is sodium phosphate and the acid and base are hydrochloric acid and sodium hydroxide. The method further comprises filtering the solution and transferring the solution to suitable receptacles, sealing the receptacles, and sterilizing the formulation. In one aspect, the formulation is sterilized by filtration and autoclaving.

Another embodiment is a formulation comprising anhydrous sodium thiosulfate made by the method described herein. Another embodiment is a means for preparing a formulation comprising anhydrous sodium thiosulfate.

Another embodiment described herein is a pharmaceutical composition of the STS formulations described herein. The pharmaceutical compositions can comprise one or more excipients, such as:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of subjects becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilization is achieved by strengthening of the protein-stabilising forces, by destabilization of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, polyethylene glycol, polyvinylpyrrolidone, protamine, or human serum albumin may be used.

(v) Anti-adsorption agents: Mainly ionic or ion-ionic surfactants or other proteins or soluble polymers are used to coat or adsorb competitively to the inner surface of the composition's container, e.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically, a monolayer of surfactant is formed at the interface just above the CMC value.

(vi) Lyophilization or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol or sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satiagum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g., Pluronic™) polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Diffusion agents: modifies the permeability of connective tissue through the hydrolysis of components of the extracellular matrix in the interstitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

The foregoing list is not meant to be exclusive, but instead merely representative of the classes of excipients and the particular excipients that may be used in pharmaceutical as described herein.

The STS formulation may be provided as a liquid, a suspension, or as a dry composition.

In one embodiment, the STS formulation is a sterile liquid composition. The formulation may be administered intravenously by either direct venipuncture or using an intravenous line.

In one embodiment, the pharmaceutical composition is a sterile solution.

In another embodiment, the STS formulation is a dry composition. Suitable methods of drying are, for example, spray drying, and lyophilization (freeze-drying). In one aspect, the STS formulation is prepared as a solution and then dried by lyophilization. In another aspect, the STS formulation is prepared as a dry composition that reconstituted immediately prior to use with sterile water for injection and then administered intravenously by either direct venipuncture or using an intravenous line.

In another embodiment, the composition is a dry or lyophilized composition that can be reconstituted with sterile water for injection, PBS, saline, or other sterile, parenterally compatible solution to produce a solution suitable for injection. In one aspect, the composition comprises about 20 mg to 32 g of anhydrous sodium thiosulfate. In one aspect, the composition comprises about 98% by mass of anhydrous sodium thiosulfate. In one aspect, the composition comprises about 1% to 2% by mass of one or more buffers. Upon addition of a specified amount of sterile water for injection, the reconstituted dry or lyophilized composition comprises about 0.5 M aqueous anhydrous sodium thiosulfate, about 0.01 M sodium phosphate, pH 6.5, and water.

Pharmaceutical compositions suitable for administration by injection include sterile aqueous solutions, suspensions, or dispersions and sterile powders or lyophilizates for the extemporaneous preparation of sterile injectable solutions or dispersion.

For intravenous administration, suitable solvents include sterile water for injection, phosphate buffered saline (PBS), physiological saline, or Ringer's solution. In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant solvent or carrier can be a solvent or dispersion medium containing, for example, water, buffers, ethanol, polyol (for example, glycerol, propylene glycol, and liquid polyethylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride, or combinations thereof in the composition.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting, or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and may contain about 0.1-75%, or contain about 1-50%, of the active ingredient. In one embodiment described herein, the composition comprises about 7.5% of the active ingredient, aqueous anhydrous sodium thiosulfate. As a dry composition suitable for reconstitution, the composition may comprise up to 98% sodium thiosulfate.

Sterile injectable solutions or suspensions can be prepared by incorporating sodium thiosulfate in the required amount in an appropriate solvent with one or a combination of ingredients, as required, followed by filtration and/or sterilization. Generally, solutions or suspensions are prepared by incorporating the active compound into a sterile vehicle such as sterile water or PBS and any excipients. In one aspect, sterilization is accomplished by autoclaving the final formulation in a vial for injection. In the case of sterile powders for the preparation of sterile injectable solutions, the preferred preparation methods are vacuum drying and freeze-drying which yield a powder of the active ingredient plus any additional excipients from a previously sterile-filtered solution thereof.

Transmucosal or transdermal administration means are also possible. Suitable compositions for transdermal application include an effective amount of a biologically active agent with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin, eyes, or joints, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well known in the art. Such may contain solubilizers, stabilizers, tonicity enhancing agents, buffers, or preservatives.

As used herein, a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Also described herein are pharmaceutical compositions and dosage forms comprising one or more agents that reduce the rate by which the compositions described herein as active ingredients will decompose. Such agents, which are referred to herein as "stabilizers," include, but are not limited to, antioxidants such as ascorbic acid, pH buffers, salts, sugars, etc.

Another embodiment described herein, is a pharmaceutical composition comprising anhydrous sodium thiosulfate. In one aspect, the composition comprises any of the formulations shown in the Tables or Examples described herein. Any of the components in the formulations described herein, shown in the Tables, or illustrated in the Examples can be increased, decreased, combined, substituted, or omitted to provide for a formulation comprising about 100% by weight. Such compositions are hereby disclosed as if they were expressly disclosed herein.

The effective amount of an active pharmaceutical ingredient to be administered therapeutically will depend, for example, upon the therapeutic context and objectives. One having ordinary skill in the art will appreciate that the appropriate dosage levels for treatment will vary depending, in part, upon the concentration of the STS formulation, the dosing regimen for which the STS formulation is being used, the route of administration, and the subject's size (body weight or body surface area) and condition (the age and general health) of the patient. Accordingly, the clinician can titer the dosage and modify the route of administration to obtain the optimal therapeutic effect.

The frequency of dosing will depend upon the pharmacokinetic parameters of the therapeutic agent incorporated into the STS formulation being used. The composition can be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The sodium thiosulfate can be administered, for example, 1×, 2×, 3×, 4×, 5×, 6×, or even more times per day. One or more doses can be administered, for example, for 1, 2, 3, 4, 5, 6, 7 days, or even longer. One or more doses can be administered, for example, for 1, 2, 3, 4 weeks, or even longer. One or more doses can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more doses can be administered at a regular interval until the subject or subject in need thereof, does not require treatment, prophylaxis, or amelioration of ototoxicity.

In one embodiment, the pharmaceutical composition described herein is administered in one or multiple doses simultaneously. For example, two or more identical doses are administered at one time. In another embodiment, two or more different doses are administered at one time. Such dual or different simultaneous doses can be used to provide an effective amount of the pharmaceutical composition to a subject in need thereof.

In another embodiment, the pharmaceutical compositions described herein may be used to treat, prevent, retard the progression of, delay the onset, ameliorate, reduce the symptoms of, or prophylaxis of ototoxicity.

In one embodiment, the STS formulation is sufficiently dosed in the composition to provide therapeutically effective amounts of sodium thiosulfate in one application. In one aspect, one application of STS formulation is sufficient for about 1 day, about 2 days, about 3 days, about 4 days, about 5 days, about 1 week, about 2 weeks, about 3 weeks, about 4 weeks, one month, 2 months, 3 months, 4 months, 6 months, 9 months, one year, 2 years, 3 years, 4 years, or even longer.

The phrases and terms "can be administered by injection," "injectable," or "injectability" refer to a combination of factors such as a certain force applied to a plunger of a syringe containing the STS formulations described herein dissolved in a liquid at a certain concentration (w/v) and at a certain temperature, a needle of a given inner diameter connected to the outlet of such syringe, and the time required to extrude a certain volume of the STS formulations from the syringe through the needle.

In one embodiment, the STS formulation is provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose STS formulations either can be used for different subjects in need thereof or is intended for use in one subject, wherein the remaining doses are stored after the application of the first dose until needed.

In another embodiment, the STS formulation is comprised in one or more containers. For liquid or suspension compositions, the container is preferably a single chamber syringe. For dry compositions, preferably the container is a dual-chamber syringe. The dry composition is provided in a first chamber of the dual-chamber syringe and reconstitution solution is provided in a second chamber of the dual-chamber syringe.

Prior to administering the dry STS formulation to a subject in need thereof, the dry composition is reconstituted. Reconstitution can take place in the container in which the dry STS formulation is provided, such as in a vial, syringe, dual-chamber syringe, ampoule, or cartridge. Reconstitution is performed by adding a predefined amount of reconstitution solution to the dry composition. Reconstitution solutions are sterile liquids, such as water for injection, phosphate buffered saline, isotonic saline, or other buffers, which may contain further excipients, such as preservatives and/or antimicrobials, such as, for example, benzylalcohol and cresol. Preferably, the reconstitution solution is sterile water for injection. Alternatively, the reconstitution solution is sterile phosphate buffered saline (PBS) or physiological saline.

Another embodiment is a method of preparing a reconstituted composition comprising a therapeutically effective amount of a STS formulation, and optionally one or more pharmaceutically acceptable excipients, the method comprising the step of contacting the composition with a volume of reconstitution vehicle. The reconstituted STS formulation may then be administered by injection or other routes.

Another embodiment is a reconstituted composition comprising a therapeutically effective amount of a STS formulation, a reconstitution vehicle, and optionally one or more pharmaceutically acceptable excipients.

Another embodiment is a pre-filled syringe comprising a solution or a suspension comprising a therapeutically effective amount of a STS formulation, and optionally one or more pharmaceutically acceptable excipients. In one aspect, the syringe is filled with between about 0.01 mL and about 5 mL of a STS formulation as described herein. In one aspect, the syringe is filled with between about 0.05 mL and about 5 mL, between about 1 mL and about 2 mL, between about 0.1 mL and about 0.15 mL, between about 0.1 mL, about 0.5 mL, between about 0.15 mL and about 0.175 mL, or about 0.5 to about 5 mL. In one embodiment, the syringe is filled with 0.165 mL of a STS formulation as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a STS formulation as described herein. A syringe is often filled with more than the desired dose to be administered to the patient, to take into account wastage due to "dead space" within the syringe and needle. There may also be a pre-determined amount of waste when the syringe is primed by the physician, so that it is ready to inject the patient.

In one embodiment, a syringe is filled with a dosage volume (e.g., the volume of medicament intended for delivery to the patent) of between about 0.01 mL and about 5 mL depending on the route of injection (e.g., between about 0.01 mL and about 0.1 mL, between about 0.1 mL and about 0.5 mL, between about 0.2 mL and about 2 mL, between about 0.5 mL and about 5 mL, or between about 1 mL and about 5 mL) of a STS formulation as described herein.

In one embodiment, when the composition is intended for injection, a syringe is filled with a dosage volume of between about 0.01 mL and about 5.0 mL of a STS formulation solution or suspension with a drug concentration of 0.1 mg/mL to 40 mg/mL as described herein. In some aspects, a syringe is filled with about 0.01 mL, about 0.02 mL, about 0.03 mL, about 0.04 mL, about 0.05 mL, about 0.06 mL, about 0.07 mL, about 0.08 mL, about 0.09 mL, about 0.1 mL, about 0.2 mL, about 0.3 mL, about 0.4 mL, about 0.5 mL, about 0.6 mL, about 0.7 mL, about 0.8 mL, about 0.9 mL, about 1 mL, about 1.2 mL, about 1.5 mL, about 1.75 mL, about 2 mL, about 2.5 mL, about 3 mL, about 4 mL, or about 5 mL of a STS formulation as described herein for delivery to a patient in need thereof.

The outlet of a syringe comprising a medicament may be reversibly sealed to maintain sterility of the medicament. This sealing may be achieved by a sealing device as is known in the art, such as a luer lock or a tamper resistant seal.

Another embodiment is a kit comprising one or more vials or pre-filled syringes comprising a solution or suspension of one or more STS formulations as described herein. In one embodiment, such a kit comprises a vial or pre-filled syringe comprising STS formulations as described herein in a blister pack or a sealed sleeve. The blister pack or sleeve may be sterile on the inside. In one aspect, vials or pre-filled syringes as described herein may be placed inside such blister packs or sleeves prior to undergoing sterilization, for example terminal sterilization. The kit may also comprise documents comprising prescribing information or instructions for use.

Such a kit may further comprise one or more needles for administration of STS formulations as described herein. Such kits may further comprise instructions for use, a drug label, contraindications, warnings, or other relevant information. One embodiment described herein is a carton or package comprising one or more vials or pre-filled syringes comprising one or more STS formulations as described herein contained within a blister pack, a syringe, a needle, and optionally documents or instructions for administration, a drug label, contraindications, warnings, or other relevant information.

A terminal sterilization process may be used to sterilize the vials or syringes and such a process may use a known process such as autoclaving, ethylene oxide, or a hydrogen peroxide ($H_2O_2$) sterilization process. Needles to be used with the syringe can be sterilised by the same method, as can kits described herein. In one aspect, a package is exposed to autoclaving or a sterilizing gas until the outside of the package is sterile. Following such a process, the outer surface of the syringe may remain sterile (while in its blister pack) for up to 6 months, 9 months, 12 months, 15 months, 18 months, 24 months or longer. Thus, in one embodiment, a pre-filed syringe as described herein (in its blister pack) may have a shelf life of up to 6 months, 9 months, 12 months, 15 months, 18 months, 24 months, or even longer. In one embodiment, less than one syringe in a million has detectable microbial presence on the outside of the syringe after 18 months of storage. In one aspect, the pre-filled syringe has been sterilised using ethylene oxide with a Sterility Assurance Level of at least $10^{-6}$. In another aspect, the pre-filled syringe has been sterilised using hydrogen peroxide with a Sterility Assurance Level of at least $10^{-6}$. Significant amounts of the sterilising gas should not enter the variable volume chamber of the syringe. The term "significant amounts" As used herein, refers to an amount of gas that would cause unacceptable modification of the STS formulation solution or suspension within the variable volume chamber. In one embodiment, the sterilization process causes ≤10% (preferably ≤5%, ≤2%, ≤1%, ≤0.5%, ≤0.1%) alkylation of the STS formulation. In one embodiment, the pre-filled syringe has been sterilised using ethylene oxide, but the outer surface of the syringe has ≤1 ppm, preferably ≤0.2 ppm ethylene oxide residue. In one embodiment, the pre-filled syringe has been sterilised using hydrogen peroxide, but the outer surface of the syringe has ≤1 ppm, preferably ≤0.2 ppm hydrogen peroxide residue. In another embodiment, the pre-filled syringe has been sterilised using ethylene oxide, and the total ethylene oxide residue found on the outside of the syringe and inside of the blister pack is ≤0.1 mg. In another embodiment, the pre-filled syringe has been sterilised using hydrogen peroxide, and the total hydrogen peroxide residue found on the outside of the syringe and inside of the blister pack is ≤0.1 mg.

Another embodiment described herein is a kit comprising sodium thiosulfate for administration to a subject. For liquid and suspension compositions, and when the administration device is simply a hypodermic syringe, the kit may comprise the syringe, a needle, and a container comprising the STS formulation for use with the syringe. In case of a dry composition, the container may have one chamber containing the dry STS composition, and a second chamber comprising a reconstitution solution. In one embodiment, the injection device is a hypodermic syringe adapted so the container with STS formulation can engage with the injection device such that the liquid, suspension, or reconstituted dry composition in the container is in fluid connection with the outlet of the injection device. Examples of administration devices include but are not limited to hypodermic syringes and pen injector devices.

Another embodiment comprises a kit comprising a needle and a container containing the STS formulation composition and optionally further containing a reconstitution solution, the container being adapted for use with the needle. In one aspect, the container is a pre-filled syringe. In another aspect, the container is dual chambered syringe. In another aspect, the STS formulation is provided as a lyophilisate in a sealed vial and a reconstitution solution is provided in another receptacle such as a sealed vial or a pre-filled syringe. An appropriate volume of the reconstitution solution is used to resuspend the lyophilisate. In another aspect, the kit comprises instructions, labels, or other written matter.

Another embodiment is a cartridge containing a composition described herein for use with a pen injector device. The cartridge may contain a single dose or plurality of doses of the STS formulation.

In another embodiment, one or more STS formulations are simultaneously administered, with each STS formulation having either separate or related biological activities.

In an alternative embodiment, the STS formulation is combined with a second biologically active compound in such way that the STS formulation is administered to a subject in need thereof first, followed by the administration of the second compound. Alternatively, the STS formulation composition is administered to a subject in need thereof after another compound has been administered to the same subject.

Another embodiment described herein is a method for reducing ototoxicity in patients (e.g., pediatric patients) having a cancer and who are receiving a platinum based chemotherapeutic for treatment of the cancer. The methods include administering an effective amount of STS to the patient. In one aspect, the STS comprises one or more of the STS formulations described herein. It was found that STS significantly reduces the risk of ototoxicity particularly in pediatric patient populations. Therefore, one embodiment, described herein is a method for reducing ototoxicity in a pediatric patient having a cancer and receiving a platinum based chemotherapeutic comprising administering an effective amount of STS to the pediatric patient. In some aspects, the pediatric patient already has incurred ototoxicity and the administration of STS reduces the amount of future ototoxicity incurred by the pediatric patient.

The risk of a pediatric patient having detectable ototoxicity, for example, hearing loss measured by the Brock scale of ≥1 is significantly reduced by treatment with STS following the administration of a cisplatinum based chemotherapeutic. The risk of ototoxicity is relevant to a pediatric patient not receiving STS. Thus, in some embodiments, the likelihood of a pediatric patient incurring any ototoxicity is reduced by STS administration by about 10% to about 100%, about 30% to about 90% or about 40% to about 70%, including each integer within the specified ranges. In some embodiments, the risk of a pediatric patient incurring any ototoxicity is reduced by STS administration by about 10%, about 20%, about 30%, about 40%, about 50%, about 60%, about 70%, about 80%, about 90%, or even about 100%. In some aspects, the risk of a pediatric patient incurring ototoxicity according to ASHA-defined hearing loss criteria is about 50%.

Similarly, treatment of a pediatric patient with STS can further reduce long-term ototoxicity in pediatric patients having a cancer and receiving a platinum based chemotherapeutic. It is known that following treatment with STS, pediatric patients can exhibit ototoxicity weeks, months, or even years following the succession of treatment with the platinum based chemotherapeutic. Thus, another embodiment described herein is a method of reducing long-term ototoxicity in a pediatric patient having a cancer and receiving a platinum based chemotherapeutic comprising administering an effective amount of sodium thiosulfate to the pediatric patient.

As described above, it is thought that platinum-based chemotherapeutic agents, such as cisplatin, exert ototoxic effects by concentrating in the aural cavity of a patient (e.g., a pediatric patient). It is further contemplated herein that STS can reduce the amount of platinum based chemotherapeutic agent in the aural cavity by binding to the agent and reducing its accumulation in the aural cavity. Another embodiment described herein is a method of reducing a concentration of cisplatin in an aural cavity of a pediatric patient having a cancer and receiving a platinum based chemotherapeutic comprising administering an effective amount of sodium thiosulfate to the pediatric patient. In some aspects, the concentration of cisplatin is reduced by in the aural cavity by about 50%, about 60%, about 70%, about 80%, about 90%, or about 100% compared to a pediatric patient receiving a platinum based chemotherapeutic and not receiving STS. In some aspects, the concentration of cisplatin is not detectable in the aural cavity. In some aspects, the patient administered STS is less susceptible to incurring ototoxicity because the amount of platinum based chemotherapeutic in the aural cavity is reduced. Methods for detecting cisplatin in the aural cavity include extracting a sample from the aural cavity and measuring the amount of cisplatin present in the sample, for example, through high performance liquid chromatography (HPLC) or other methods known in the art.

The methods described herein are also useful for preventing or inhibiting ototoxicity in a pediatric patient having a cancer and who is receiving a platinum based chemotherapeutic for treatment of the cancer. It was found that pediatric patients are particularly susceptible to incurring ototoxicity and prophylactically treating the pediatric patient can reduce the ototoxicity in the pediatric patient. Therefore, another embodiment described herein is a method of prophylactically treating a pediatric patient having a cancer and receiving a platinum based chemotherapeutic with an effective amount of STS, wherein the treatment reduces a likelihood of the pediatric patient incurring ototoxicity.

It has been determined that certain genetic variations can cause an increased likelihood of a pediatric patient having ototoxicity and the severity of ototoxicity in the patient. The genes TPMT, COMT, and ABCC3 have been shown to put pediatric patients at a greater risk for incurring ototoxicity. See Ross et al., "Genetic variants in TPMT and COMT are associated with hearing loss in children receiving cisplatin chemotherapy," *Nat. Genet.* 41: 1345-1349 (2009); Pussegoda et al., "Replication of TPMT and ABCC3 genetic variants is highly associated with cisplatin-induced hearing loss in children," *Clin. Pharmacol. Ther.* 94: 243-251 (2013). In addition, it has more recently been shown that single nucleotide polymorphism in the ACYP2 gene at the locus rs1872328 are associated with cisplatin-based ototoxicity. See Xu, K. et al., "Common variants in ACYP2 influence susceptibility to cisplatin-induced hearing loss," *Nat. Genet.* 47(3): 263-266 (2015). Thus, in some embodiments a pediatric patient receiving a cisplatin based chemotherapeutic is identified as being at high risk for having a genetic variation in one or more of the genes TPMT, COMT, ABCC3, and ACYP2 and treated with STS to reduce the likelihood, prevent, inhibit, or treat ototoxicity.

In some embodiments described herein, the pediatric patient has a cancer and is receiving a platinum based chemotherapeutic. In some other embodiments, the pediatric patient does not yet have a diagnosed cancer but is being treated with a platinum based chemotherapeutic. Any platinum-based drug would be expected to be scavenged by STS and reduce ototoxicity. Thus, in some embodiments, the platinum based chemotherapeutic comprises cisplatin, carboplatin, oxaliplatin, nedaplatin, triplatin tetranitrate, phenanthriplatin, picoplatin, and satraplatin. In some aspects, the platinum based chemotherapeutic is cisplatin.

The amount of platinum based chemotherapeutic that a pediatric patient is receiving is determined by the treating physician, the type of disease or cancer that is being treated, and the age or weight of the pediatric patient. In some aspects, the amount of platinum based chemotherapeutic (e.g., cisplatin) per cycle of administration is about 1 mg/kg to about 5 mg/kg, including each integer within the specified range. In some aspects, the amount of platinum based chemotherapeutic (e.g., cisplatin) per cycle of administration is about 10 mg/m$^2$ to about 300 mg/m$^2$, 10 mg/m$^2$ to about 100 mg/m$^2$, or about 40 mg/m$^2$ to about 80 mg/m$^2$, including each integer within the specified ranges.

Many cancers are treated with platinum-based chemotherapeutics in pediatric patients, for which STS may be administered. In some aspects of the embodiments described herein, a pediatric patient has a cancer that is being treated with a platinum based chemotherapeutic followed by STS, wherein the cancer is localized or disseminated. In some aspects, the cancer is low-risk, medium risk, or high risk (e.g., metastatic) cancer. In some aspects, the cancer is low-risk or medium-risk. In some aspects, the cancer being treated with a platinum based chemotherapeutic is localized and is not disseminated or metastatic. Non-limiting and exemplary cancers that can be treated with a platinum based chemotherapeutic followed by STS comprise germ cell tumors (e.g., testicular cancer or ovarian cancer), hepatoblastoma, medulloblastoma, neuroblastoma, and osteosarcoma. In some aspects, a pediatric patient has a hepatoblastoma cancer and is being treated with a platinum based chemotherapeutic and STS. In some aspects, a pediatric patient has a low-risk or medium-risk hepatoblastoma cancer and is being treated with a platinum based chemotherapeutic and STS.

In some embodiments, the STS is administered to a pediatric patient receiving treatment with a platinum-based chemotherapeutic agent prior to, concurrently with, or after the administration of the platinum based chemotherapeutic. In some aspects, the STS is administered 0 minutes or about 5 minutes to about 96 hours after the administration of the platinum based chemotherapeutic, including each integer of time within the specified range. In some aspects, the STS is administered about 30 minutes to about 24 hours, about 1 hour to about 24 hours, about 1 to about 12 hours, about 1 hour to about 8 hours, or about 4 hours to about 7 hours after the administration of the platinum based chemotherapeutic, including each integer of time within the specified ranges. In one aspect, the STS is administered about 6 hours after the administration of the platinum based chemotherapeutic.

The administration of STS may be carried out in any way that is known for administering STS. For example, STS may be administered parenterally or enterally. If administered parenterally, the STS can be administered intravenously (IV), subcutaneously (SC), or intramuscularly (IM). Enteral administration includes oral, sublingual, or rectal. In one embodiment, the STS is administered intravenously.

An effective amount of STS is an amount of STS, which prevents, reduces, or inhibits ototoxicity in a pediatric patient receiving a platinum based chemotherapeutic. In some embodiments, the amount of STS administered is about 0.5 g/m$^2$ to about 50 g/m$^2$, about 1 g/m$^2$ to about 25 g/m$^2$ or 15 g/m$^2$ to about 25 g/m$^2$, including each integer within the specified ranges. In some embodiments, the amount of STS administered is about 1 g/m$^2$, about 2 g/m$^2$, about 4 g/m$^2$, about 6 g/m$^2$, about 8 g/m$^2$, about 10 g/m$^2$, about 15 g/m$^2$, about 20 g/m$^2$, about 25 g/m$^2$, about 30 g/m$^2$, about 40 g/m$^2$, or about 50 g/m$^2$. The effective amount of STS is administered prior to, concomitantly with, or following each cycle of platinum based chemotherapy.

Some additional embodiments described herein are dosing regimens for treating a cancer in a pediatric patient, which include administering a platinum based chemotherapeutic and STS. One embodiment is a dosing regimen for treating hepatoblastoma in a pediatric patient that includes administering a dose of about 1 mg/kg to about 5 mg/kg or about 10 mg/m$^2$ to about 300 mg/m$^2$ per cycle of a platinum based chemotherapeutic, including each integer within the recited range; and also administering about 5 g/m$^2$ to about 25 g/m$^2$ of STS per cycle of the platinum based chemotherapeutic, including each integer within the specified ranges. In one aspect, the STS is administered from about 2 hours to about 6 hours after the administration of the platinum based chemotherapeutic, including each integer within the recited range.

The measurement of ototoxicity following administration of the platinum based chemotherapeutic and STS should be carried out after a period time following the last treatment with the platinum based chemotherapeutic and STS. In some aspects, the ototoxicity is measured after a time period of at least 3 days to about 3 months, 1 week to about 3 months, 1 week to about 2 months, or 1 week to about 4 weeks following the last treatment with the platinum based chemotherapeutic and STS, including each integer within the specified ranges of time. In one aspect, the ototoxicity is measured after a time period of at least 4 weeks from the last treatment with the platinum based chemotherapeutic and STS.

The measurement of ototoxicity following administration of the platinum based chemotherapeutic and STS can be carried out multiple times and up to years following the last administration of STS and the platinum based chemotherapeutic. Audiometric methods for measuring hearing loss are well known to those of ordinary skill in the art and are used in conjunction with various scales to assess ototoxicity. Assessing ototoxicity allows, for example, the assessment of any potential ototoxicity or long-term prevention of ototoxicity by STS. The assessment of ototoxicity can be determined by one or more criteria known in the art. For example, ototoxicity may include assessment by the tinnitus functional index, Brock grading, Children's Cancer Group 1996 study scale, Children's Hospital Boston scale, the Chang and Chinosornvatana scale, the American Speech-Language-Hearing Association criteria, the Common Terminology Criteria for Adverse Events scale (CTCAE pediatric grading), or the International Society of Pediatric Oncology Boston Ototoxicity Scale or a combination of these scales.

See Gurney, et al., "Oncology," *J. Clin. Onc.* 30(19): 2303-2306 (2012). The measurement of hearing function should in most cases be completed prior to treatment with an ototoxic drug such as a cisplatin or another platinum based chemotherapeutic. This establishes a baseline measure of hearing function to which any potential ototoxic effects can be compared. Thus, changes in hearing or increase or decrease in ototoxicity is computed relative to baseline measures prior to the patient receiving a platinum based chemotherapeutic or sodium thiosulfate or both.

The Brock scale is defined as follows: a <40 dB hearing loss at all frequencies, which indicates a grade 0 or minimal hearing loss; a ≥40 dB hearing loss at 8,000 Hz only, which indicates a grade 1 or mild hearing loss; a ≥40 dB hearing loss at 4,000 Hz and above, which indicates a grade 2 or moderate hearing loss; a ≥40 dB hearing loss at 2,000 Hz and above, which indicates a grade 3 or marked hearing loss; or a ≥40 dB hearing loss at 1,000 Hz and above, which indicates a grade 4 or severe hearing loss.

The CTCAE scale is based on hearing at 1, 2, 3, 4, 6, and 8 kHz. Grade 1 is a threshold shift >20 dB at 8 kHZ in at least 1 ear; Grade 2 is a threshold shift >20 dB at 4 kHz and above in at least 1 ear; Grade 3 is hearing loss sufficient to indicate therapeutic intervention including hearing aids, a threshold shift >20 dB at 3 kHz and above in at least 1 ear; speech and language svcs indicated; and grade 4 is the audiologic indication of cochlear implant and speech and language svcs indicated.

The Children's Cancer Group 1996 scale is defined as follows: ≥40 dB HL loss at 6,000 and/or 8,000 Hz is indicative of grade 1, >25 dB HL loss at 3,000 and/or 4,000 Hz is indicative of grade 2, >25 dB HL loss at 2,000 Hz is indicative of grade 3; and a ≥40 dB HL loss at 2,000 Hz is indicative of grade 4. Children's Hospital Boston scale is defined as follows: <20 dB hearing loss at frequencies 500-8,000 Hz; no functional hearing loss; >20 dB hearing loss above 4,000 Hz; functional loss: slight hearing loss that may result in decreased musical appreciation indicative of a grade 1; >20 dB hearing loss at 4,000 Hz and above; functional loss: educationally significant hearing loss indicative of grade 2; >20 dB hearing loss at 2,000 Hz and above; functional loss: severe hearing loss requiring hearing aids indicative of grade 3.

The Chang and Chinosornvatana scale is defined as ≤20 dB at 1, 2, and 4 kHz is indicative of normal hearing; (1a) ≥40 dB at any frequency 6 to 12 kHz; (1b) >20 and <40 dB at 4 kHz is indicative of grade 1a and 1b, respectively; (2a) ≥40 dB at 4 kHz and above; (2b) >20 and <40 dB at any frequency below 4 kHz is indicative of grade 2a and 2b, respectively; ≥40 dB at 2 or 3 kHz and above is indicative of grade 3; and ≥40 dB at 1 kHz and above is indicative of grade 4.

The American Speech-Language-Hearing Association criteria is defined as (1) ≥20 dB decrease at any one frequency; (2) ≥10 dB decrease at two or more adjacent frequencies; or (3) loss of response at three adjacent frequencies at which responses were previously obtained. The ASHA further specifies that a significant change in hearing sensitivity must be confirmed by repeat testing to be considered valid.

International Society of Pediatric Oncology Boston Ototoxicity Scale is defined as ≤20 dB HL at all frequencies is indicated to be normal hearing; >20 dB HL (e.g., 25 dB HL or greater); SNHL above 4,000 Hz (e.g., 6 or 8 kHz) is indicated to be grade 1; >20 dB HL SNHL at 4,000 Hz and above is indicated to be grade 2; >20 dB HL SNHL at 2,000 Hz or 3,000 Hz and above is indicated to be grade 3; and >40 dB HL (e.g., 45 dB HL or more) SNHL at 2,000 Hz is indicated to be grade 4.

The tinnitus functional index is a questionnaire-based index that quantitates the severity of tinnitus symptoms. See Henry J A et al., *Audiology Today* 26(6): 40-48 (2014). The index is defined as follows: a mean score of 14 (range of 0-17) is no tinnitus, a mean score of 21 indicates a low levels of tinnitus; a mean score of 42 is a moderate tinnitus; a mean score of 65 is high levels of tinnitus, and a mean score of 78 is large levels of tinnitus. Ranges can be broken down into <25 is relatively mild tinnitus or no tinnitus, 25-50 indicates significant problems with tinnitus, and >50 indicates levels of tinnitus that require aggressive intervention.

In some embodiments, the ototoxicity is measured by measuring hearing loss at one or more frequencies comprising 500 Hz, 1,000 Hz, 2,000 Hz, 4,000 Hz, or 8,000 Hz or a combination of frequencies thereof, wherein a change in hearing is computed relative to baseline measures prior to the patient receiving a platinum based chemotherapeutic or sodium thiosulfate or both. In some aspects, an increase in ototoxicity can be determined as a reduction in hearing measured by a 20 dB loss at a single frequency; a reduction in hearing measured by a 10 dB loss at two consecutive frequencies; or a loss of response at three consecutive test frequencies where responses were previously obtained. In some further aspects, an increase in ototoxicity is measured as a reduction in bilateral high-frequency hearing characterized by: a <40 dB hearing loss at all frequencies, which indicates a grade 0 or minimal hearing loss; a ≥40 dB hearing loss at 8,000 Hz only, which indicates a grade 1 or mild hearing loss; a ≥40 dB hearing loss at 4,000 Hz and above, which indicates a grade 2 or moderate hearing loss; a ≥40 dB hearing loss at 2,000 Hz and above, which indicates a grade 3 or marked hearing loss; or a ≥40 dB hearing loss at 1,000 Hz and above, which indicates a grade 4 or severe hearing loss. In still some further aspects, an increase in ototoxicity is measured as a reduction in hearing characterized by: a ≤20 dB hearing loss at all frequencies, which indicates a grade 0 hearing loss; a >20 dB HL above 4,000 Hz, which indicates a grade 1 hearing loss; a >20 dB HL at 4,000 Hz and above, which indicates a grade 2 hearing loss; a >20 dB HL at 2,000 Hz or 3,000 Hz, which indicates a grade 3 hearing loss; or a >40 dB HL at 2,000 Hz and above, which indicates a grade 4 hearing loss. In some other aspects, an increase in ototoxicity can be measured by a reduction in a tinnitus functional index.

The administration of STS to pediatric patients being treated with a platinum based chemotherapeutic was found to not exacerbate renal or other toxicities. Thus, in some aspects, patients receiving STS do not experience more severe or an increased incidence rate of adverse events compared to patients not administered STS. These adverse events comprise grade 3 or grade 4 neutropenia, reduced glomerular filtration rates, increased serum creatinine, infection, hypomagnesemia, hypernatremia, vomiting, or nausea. In some other aspects, pediatric patients administered STS do not have a reduction in relapse free survival or overall survival compared to patients not administered STS.

The methods described herein are well suited for reducing or preventing ototoxicity or reducing the likelihood of incurring ototoxicity in any pediatric patient of any age. Therefore, in some embodiments described the pediatric patient being treated following the methods described herein may be a new born or the pediatric patient may about 1 month old, about 2 months old, about 3 months old, about 4 months old, about 5 months old, about 6 months old, about 7 months old, about 8 months old, about 9 months old, about 10 months old, about 11 months old, about 12 months old, about 1 year old, about 1.5 years old, about 2 years old, about 2.5 years old, about 3 years old, about 3.5 years old, about 4 years old, about 4.5 years old, about 5 years old, about 5.5 years old, about 6 years old, about 6.5 years old, about 7 years old, about 7.5 years old, about 8 years old, about 8.5 years old, about 9 years old, about 9.5 years old, about 10 years old, about 10.5 years old, about 11 years old, about 11.5 years old, about 12 years old, about 12.5 years old, about 13 years old, about 13.5 years old, about 14 years old, about 14.5 years old, about 15 years old, about 15.5 years old, about 16 years old, about 16.5 years old, about 17 years old, about 17.5 years old, about 18 years old, about 18.5 years old, about 19 years old, about 19.5 years old, about 20 years old, about 20.5 years old, or about 21 years old. In some aspects, the pediatric patient is about 12 years of age or less, about 5 years of age or less, about 2 years of age or less, or about 1 year of age or less.

Indications and Usage

In one embodiment, sodium thiosulfate for injection as described herein is indicated for the prevention of ototoxicity induced by cisplatin (CIS) chemotherapy in patients 1 month to <18 years of age with localized, non-metastatic, solid tumors.

In one embodiment, sodium thiosulfate for injection as described herein is administered as a 15-minute infusion, 6 hours after the completion of each CIS administration, when CIS is infused for no longer than 6 hours. In one aspect, the recommended dose of sodium thiosulfate for injection as described herein for the prevention of CIS-induced ototoxicity is weight-based and normalized to body surface area as shown below.

| Subject Body Weight | Dose of STS for Injection | Volume of STS for Injection |
|---|---|---|
| >10 kg | 12.8 g/m² | 160 mL/m² |
| 5 to 10 kg | 9.6 g/m² | 120 mL/m² |
| <5 kg | 6.4 g/m² | 80 mL/m² |

Dosage Forms and Strengths

Sodium thiosulfate for injection as described herein is a sterile solution containing 80 mg/mL (8 g/100 mL) of sodium thiosulfate for intravenous (IV) administration in a single-use vial.

Sodium thiosulfate for injection as described herein is administered as a 15-minute infusion, 6 hours after the completion of each CIS administration, when CIS is infused for no longer than 6 hours. Pre-treatment with antiemetics is recommended to reduce the incidence of nausea and vomiting.

The timing of sodium thiosulfate for injection administration relative to CIS chemotherapy is critical, because earlier treatment may reduce CIS efficacy, and later treatment may not be as effective in preventing ototoxicity.

Sodium thiosulfate for injection should only be administered following CIS infusions of 1 to 6 hours. Do not use sodium thiosulfate for injection if the CIS infusion exceeds 6 hours, or if a subsequent CIS infusion is planned within 6 hours.

| CIS Infusion | | Delay | | STS Infusion | | Minimum time to next CIS Infusion |
|---|---|---|---|---|---|---|
| 1-6 hrs | ⇒ | 6 hrs | ⇒ | 15 min | ⇒ | 6 hrs |

Contraindications

Sodium thiosulfate for injection as described herein is contraindicated: in patients with a known hypersensitivity to sodium thiosulfate (STS) or any of the inactive ingredients in sodium thiosulfate for injection; and in neonates under the age of 1 month due to the risk of hypernatremia.

DESCRIPTION

Sodium thiosulfate anhydrous, the active ingredient, is an inorganic salt with reducing agent properties. It is a white to off-white crystalline solid, that is soluble in water, but insoluble in alcohol. The aqueous solution is practically neutral with a pH ranging from 6.5 to 9.0. The molecular formula is $Na_2S_2O_3$. It has a molecular weight of 158.11 g/mol. The structural formula is:

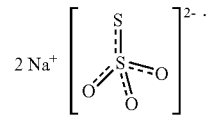

Sodium thiosulfate for injection as described herein is a sterile, preservative-free, clear solution for intravenous use. Each vial contains 80 mg/mL sodium thiosulfate anhydrous (United States Pharmacopeia, USP), water for injection (USP), boric acid or sodium phosphate as a buffer component, and sodium hydroxide and/or hydrochloric acid for pH adjustment.

Mechanism of Action

Cisplatin-induced ototoxicity is caused by irreversible damage to hair cells in the cochlea. The cochlea is very sensitive to oxidative stress, which has been shown to be involved in CIS induced hearing loss. The mechanism of STS protection against ototoxicity is not fully understood, but may include increasing levels of endogenous antioxidants, scavenging reactive oxygen species, and direct interaction between CIS and the thiol group in STS. STS has the ability to enter cells at least partly through the sodium sulfate cotransporter 2 and can cause intracellular effects such as the increase in antioxidant glutathione levels and inhibition of intracellular oxidative stress.

Pharmacodynamics

STS prevented ototoxicity in at doses equivalent to 6.4 to 12.8 g/m² sodium thiosulfate for injection. In preliminary clinical studies, lower STS dose levels (equivalent to 5.1 g/m² sodium thiosulfate for injection) resulted in low maximum plasma levels (3.9 mM) and did not show hearing protection.

The 6-hour delay of STS treatment after CIS chemotherapy is important to circumvent potential interference with the anti-tumor activity of CIS, which is supported by data from non-clinical studies and preliminary clinical studies. During CIS infusion, bioactive unbound CIS distributes to cancer cells; it is cleared through renal excretion and rapid binding to proteins leading to inactivation of its tumoricidal activity. The initial decline of unbound platinum in plasma is rapid, with a half-life ranging from 0.6 to 1.35 hours. Together with the fact that STS distribution is largely limited to extracellular spaces, administration of sodium thiosulfate for injection 6 hours after completion of each CIS infusion should prevent a tumor protective effect of STS. As shown in studies, treatment 6 hours after completion of each CIS infusion did not affect survival.

Based on the half-life of STS in plasma, a negligible amount remains 6 hours after completion of an STS infusion. Therefore, subsequent CIS infusions should be administered no sooner than 6 hours after the completion of a sodium thiosulfate infusion to avoid a pharmacodynamic interaction.

A 12.8 g/m² dose of sodium thiosulfate for injection delivers a sodium load of 162 mmol/m². Doses of STS equivalent to this resulted in a small, transient increase in serum sodium levels. When evaluated using non-compartmental pharmacokinetic analysis at the recommended sodium thiosulfate for injection dose levels, this transient increase in sodium was independent of age, body surface area, body weight, total daily STS dose, or CIS cycle.

Pharmacokinetics

Absorption

STS is poorly absorbed after oral administration and has to be administered intravenously. At the end of an STS intravenous infusion, plasma levels of STS are maximal and decline rapidly thereafter with a half-life of approximately 20 to 50 minutes. A return to pre-dose levels occurs within 3 to 6 hours after infusion. More than 95% of STS excretion in urine occurs within the first 4 hours after administration. There is no plasma accumulation when STS is administered on 2 consecutive days.

In children and adults, the maximum STS plasma levels after a 15-minute infusion of a dose equivalent to 12.8 g/m² sodium thiosulfate for injection was approximately 13.3 mM. STS plasma levels change in a dose proportional manner. Age did not appear to influence the maximum plasma levels of STS or the decline afterwards. A population pharmacokinetic model incorporating growth and maturation variables for the pediatric population showed that the predicted STS plasma levels at the end of infusion were consistent across the recommended sodium thiosulfate for injection dose levels for the indicated age and body weight ranges.

Distribution

STS does not bind to human plasma proteins. STS is an inorganic salt and thiosulfate anions do not readily cross membranes. Hence, the volume of distribution appears largely confined to extracellular spaces and estimated at 0.23 L/kg in adults. In animals, STS has been found to distribute to the cochlea. Distribution across the blood brain barrier or placenta appears absent or limited. Thiosulfate is an endogenous compound ubiquitously present in all cells and organs. Endogenous serum thiosulfate levels were 5.5±1.8 µM in adult volunteers.

Elimination

Metabolism: Metabolites of STS have not been determined as part of clinical studies. Thiosulfate is an endogenous intermediate product of sulfur-containing amino acid metabolism. Thiosulfate metabolism does not involve CYP enzymes; it is metabolized through thiosulfate sulfur transferase and thiosulfate reductase activity to sulfite, which is rapidly oxidized to sulfate.

Excretion: STS (thiosulfate) is excreted through glomerular filtration. After administration, STS (thiosulfate) levels in urine are high, and approximately half of the STS dose is retrieved unchanged in urine, nearly all excreted within the first 4 hours after administration. STS renal clearance related well with inulin clearance as a measure for the GFR.

Excretion of endogenously produced thiosulfate in bile was very low and did not increase after STS administration. No mass balance studies have been performed, but it is expected that non renal clearance will mainly result in renal excretion of sulfates. A small part of the sulfane sulfur of STS may become part of endogenous cellular sulfur metabolism.

Drug Product and Storage and Handling

Sodium thiosulfate for injection is supplied as 100 mL of a clear, colorless, sterile solution in flint glass vials with 20-mm stoppers and capped with aluminum overseals. Each 100 mL of sodium thiosulfate for injection contains sodium thiosulfate, anhydrous (80 mg per mL) for intravenous administration (8 g of STS per vial).

Sodium thiosulfate for injection should be stored at controlled room temperature, between 15° C. and 30° C.

It will be apparent to one of ordinary skill in the relevant art that suitable modifications and adaptations to the compositions, formulations, methods, processes, reactions, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Synthesis Process

An overview of the synthesis process is shown in FIG. 1. The synthesis of sodium thiosulfate (wet) was accomplished by reacting 1.0 mole equivalent of aqueous sodium sulfite with 1.1 mole equivalents of elemental sulfur in the presence of 0.00013 mole equivalents of cetylpyridinium chloride (CPC) at 90° C. for up to 3 hr as shown in Scheme I.

Scheme I

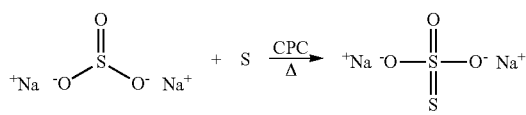

In some instances, the reaction was heated to about 90° C. and was completed upon reaching 90° C. Without being bound by any theory, the reaction rate appears to depend on the size, surface area, and solubility of the sulfur (e.g., fine powder reacts more rapidly than flakes). Once the reaction was complete, the mixture was cooled to 25° C., filtered through a 10 μm filter, and transferred to a crystallization vessel. The sodium thiosulfate solution was then cooled to less than 2° C., and acetone was slowly added over at least 1 h while maintaining a temperature of <2° C. (except during the initial nucleation where a 5-7° C. exotherm was observed). The slurry was then held at <2° C. for at least 0.5 h and stepwise transferred to a filter dryer in portions. The slurry was filtered to the point where the filtrate drops just below the level of the cake after each portion of slurry was added; this process minimized cracking of the resulting cake. The cake was then washed twice with acetone and filtered until no liquid exited. The resulting cake of "wet sodium thiosulfate" was then dried at 45° C. overnight while mixing under vacuum. The term "wet sodium thiosulfate" as used herein refers to sodium thiosulfate that has not been dehydrated.

Dehydration

Filtered methanol was used to charge a crystallization vessel and heated to 60° C. This warm methanol was then transferred into a filter dryer containing the overnight-dried "wet sodium thiosulfate" cake. The cake was slurried with the hot methanol and the filtrate was removed by pressure. A second charge of hot methanol was added, mixed, and the filtrate removed. This was followed by two additional washes with ambient temperature methanol and vacuum drying at 55° C. overnight. This process produced anhydrous sodium thiosulfate.

Example 2

Milling

Some batches of the anhydrous sodium thiosulfate were milled using a jet mill to a particle size distribution of 50% of the population, $d_{50}$, of 10-20 μm. The unmilled anhydrous sodium thiosulfate synthesized as described herein has a particle size distribution of 50-75 μm. Without being bound by any theory, milling increased the surface area of the sodium thiosulfate particles and was believed to permit enhanced evaporation of any residual solvent(s).

Example 3

Analysis

The dried and/or milled anhydrous sodium thiosulfate was collected at stored at ambient temperature. Samples were analyzed for sodium sulfite, sulfur, acetone, and methanol levels among other trace elements using HPLC, inductively coupled plasma mass spectrometry (ICP-MS), FTIR spectroscopy, and X-ray powder diffraction. Specifications and representative data for anhydrous sodium thiosulfate synthesized as described using the foregoing methods are shown in Table 4.

TABLE 4

Specifications and Representative STS Parameters

| Parameter | Specification | Result |
|---|---|---|
| Appearance | White to off-white solid, free of particulate | White to off-white solid, free of particulate |
| Cadmium | ≤0.10 μg/g | ≤0.05 μg/g |
| Lead | ≤0.25 μg/g | ≤0.125 μg/g |
| Arsenic | ≤0.75 μg/g | ≤0.375 μg/g |
| Mercury | ≤0.15 μg/g | ≤0.075 μg/g |
| Cobalt | ≤0.25 μg/g | ≤0.125 μg/g |
| Vanadium | ≤0.50 μg/g | ≤0.25 μg/g |
| Nickel | ≤1.00 μg/g | ≤0.50 μg/g |

TABLE 4-continued

Specifications and Representative STS Parameters

Figure 2A:
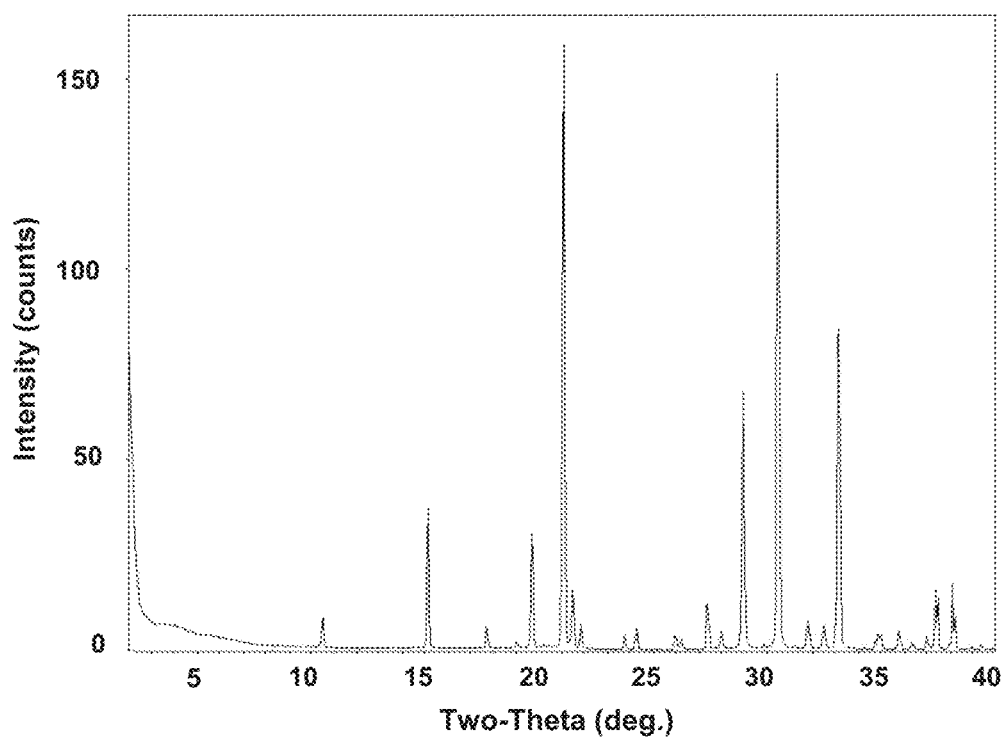
FIG. 2A shows X-ray powder diffraction pattern for anhydrous sodium thiosulfate synthesized as described herein. Peaks are shown in Table 5.
Figure 2B:
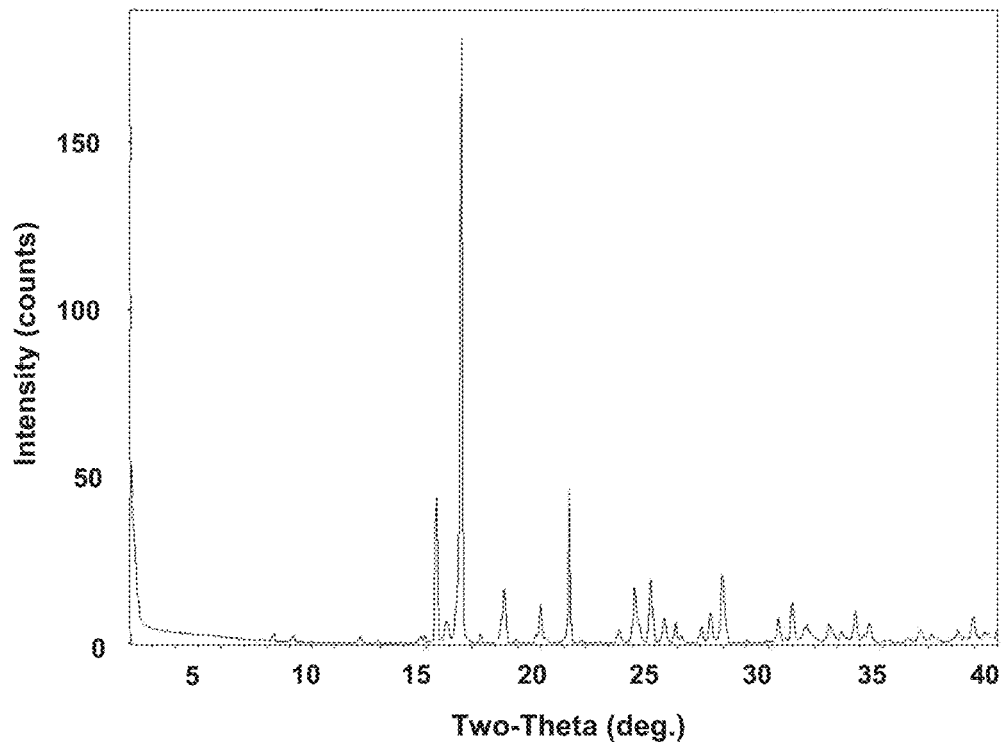
FIG. 2B shows X-ray powder diffraction pattern for sodium thiosulfate pentahydrate. Peaks are shown in Table 6.
Figure 3:
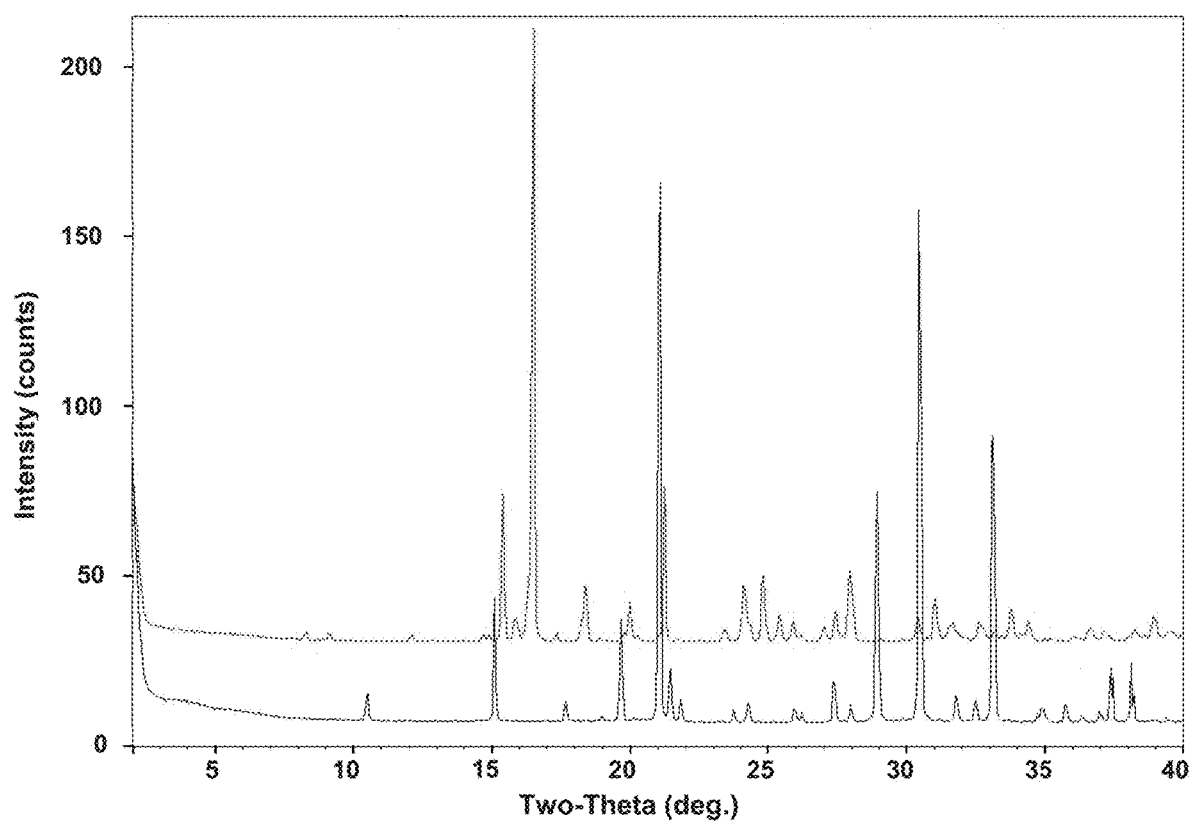
FIG. 3 shows overlayed X-ray powder diffraction patterns for sodium thiosulfate pentahydrate (top pattern) and anhydrous sodium thiosulfate synthesized as described herein (bottom pattern).

| Parameter | Specification | Result |
|---|---|---|
| Lithium | ≤12.5 μg/g | ≤6.25 μg/g |
| Antimony | ≤4.50 μg/g | ≤2.25 μg/g |
| Copper | ≤15.0 μg/g | ≤7.5 μg/g |
| Methanol | ≤1500 ppm | 841 ppm |
| Water | ≤3% (w/w) | 0.07% (w/w) |
| FTIR Indentification | Conforms to known reference spectrum | Conforms |
| XRPD Results | Report result | See FIGS. 2 and 3. |
| Differential Scanning Calorimetry | | |
| Onset Temp | Report result | 330.6° C. |
| Peak Temp | Report result | 334.0° C. |
| Heat Flow | Report result | −122.73 J/g |
| Total Aerobic Microbial Count | ≤100 CFU | ≤1 CFU |
| Total Combined Yeast/Mold Count | ≤100 CFU | ≤1 CFU |
| HPLC | Retention time conforms to reference standard | Conforms |
| Assay, as is | 98-102% (w/w) | 98.50% |
| Total Impurities | ≤1.5% (w/w) | ≤1.5% (w/w) |

Example 4

X-Ray Powder Diffraction Characterization

Samples of anhydrous sodium thiosulfate as described herein or sodium thiosulfate pentahydrate were analyzed by X-Ray Powder Diffraction (XRPD). Between 2 and 50 mg of sample were placed in a zero background holder coated with a thin layer of petroleum jelly and leveled with a glass plate. XRPD data was acquired using a Bruker D8 X-ray Diffractometer from 2° to 40° 2θ with a 0.05° step size (1 sec/step) with copper Kα radiation (40 kV). The sample was rotated at 15 RPM during acquisition. Peak picking was performed in Materials Data Jade 9.7.0 software.

The XRPD patterns for anhydrous sodium thiosulfate or sodium thiosulfate pentahydrate are shown in FIGS. 2A and 2B, respectively; XRPD peaks are listed in Tables 5 and 6, respectively. Significant peaks are shown in bold. An overlay of the anhydrous sodium thiosulfate pattern in 2A (bottom pattern) and sodium thiosulfate pentahydrate pattern in 2B (top pattern) is shown in FIG. 3.

TABLE 5

Anhydrous Sodium Thiosulfate X-ray Powder Diffraction Peaks

| 2-theta (deg.) | d(Å) | Height | Height Percent (%) |
|---|---|---|---|
| 10.523 | 8.4000 | 7.6 | 4.8 |
| 15.138 | 5.8481 | 36.6 | 23.2 |
| 17.712 | 5.0036 | 5.9 | 3.7 |
| 19.021 | 4.6620 | 1.8 | 1.1 |
| 19.702 | 4.5023 | 29.8 | 18.9 |
| 20.199 | 4.3927 | 0.5 | 0.3 |
| 21.086 | 4.2099 | 157.9 | 100 |
| 21.490 | 4.1315 | 14.3 | 9.1 |
| 21.848 | 4.0647 | 5.2 | 3.3 |
| 23.767 | 3.7407 | 3.7 | 2.3 |
| 24.288 | 3.6617 | 5.7 | 3.6 |
| 25.986 | 3.4261 | 3.8 | 2.4 |
| 26.260 | 3.3909 | 2.8 | 1.7 |
| 27.402 | 3.2522 | 11.8 | 7.4 |
| 28.012 | 3.1828 | 4.6 | 2.9 |
| 28.962 | 3.0805 | 67.5 | 42.8 |
| 30.465 | 2.9318 | 145.4 | 92.1 |
| 31.814 | 2.8105 | 6.8 | 4.3 |
| 32.516 | 2.7514 | 6.0 | 3.8 |

TABLE 5-continued

Anhydrous Sodium Thiosulfate X-ray Powder Diffraction Peaks

| 2-theta (deg.) | d(Å) | Height | Height Percent (%) |
|---|---|---|---|
| 33.147 | 2.7005 | 84.0 | 53.2 |
| 34.740 | 2.5802 | 2.8 | 1.7 |
| 34.916 | 2.5676 | 4.0 | 2.5 |
| 35.786 | 2.5071 | 4.5 | 2.9 |
| 36.365 | 2.4686 | 1.7 | 1.1 |
| 37.029 | 2.4258 | 3.1 | 2.0 |
| 37.396 | 2.4028 | 11.2 | 7.1 |
| 37.499 | 2.3964 | 9.2 | 5.8 |
| 38.157 | 2.3566 | 11.0 | 7.0 |
| 38.260 | 2.3505 | 5.9 | 3.8 |

Significant peaks are bolded.
Peaks unique to or prominent in the anhydrous sodium thiosulfate form are: 10.52, 15.13, 19.70, 21.49, 21.84, 28.96, 30.46, 33.15, 37.40, and 38.16.

TABLE 6

Sodium Thiosulfate Pentahydrate X-ray Powder Diffraction Peaks

| 2-theta (deg.) | d(Å) | Height | Height Percent (%) |
|---|---|---|---|
| 8.344 | 10.5876 | 2.4 | 1.3 |
| 9.189 | 9.6164 | 2.6 | 1.5 |
| 12.129 | 7.2914 | 1.8 | 1.0 |
| 14.747 | 6.0022 | 2.1 | 1.2 |
| 14.946 | 5.9225 | 2.4 | 1.3 |
| 15.438 | 5.7351 | 41.6 | 23.3 |
| 15.906 | 5.5674 | 6.2 | 3.5 |
| 16.534 | 5.3573 | 178.8 | 100 |
| 17.388 | 5.0961 | 1.6 | 0.9 |
| 18.408 | 4.8159 | 16 | 8.9 |
| 18.961 | 4.6767 | 0.5 | 0.3 |
| 19.790 | 4.4825 | 1.2 | 0.7 |
| 20.014 | 4.433 | 11.1 | 6.2 |
| 20.251 | 4.3816 | 1.7 | 1.0 |
| 21.249 | 4.1780 | 42.4 | 23.7 |
| 23.448 | 3.7909 | 3.6 | 2.0 |
| 24.123 | 3.6863 | 16.2 | 9.1 |
| 24.35 | 3.6524 | 5.6 | 3.1 |
| 24.847 | 3.5805 | 18.7 | 10.4 |
| 25.435 | 3.4991 | 7.0 | 3.9 |
| 25.933 | 3.4329 | 5.5 | 3.1 |
| 26.189 | 3.4000 | 1.0 | 0.5 |
| 27.049 | 3.2938 | 3.6 | 2.0 |
| 27.462 | 3.2453 | 9.1 | 5.1 |
| 27.974 | 3.1870 | 19.4 | 10.9 |
| 30.438 | 2.9343 | 5.9 | 3.3 |
| 31.045 | 2.8783 | 11.2 | 6.2 |
| 31.691 | 2.8212 | 4.4 | 2.4 |
| 32.654 | 2.7401 | 4.7 | 2.6 |
| 33.198 | 2.6964 | 1.8 | 1.0 |
| 33.805 | 2.6494 | 6.9 | 3.9 |
| 34.151 | 2.6233 | 1.2 | 0.7 |
| 34.400 | 2.6049 | 4.0 | 2.2 |
| 35.016 | 2.5605 | 0.1 | 0.0 |
| 35.243 | 2.5445 | 0.1 | 0.1 |
| 36.097 | 2.4862 | 0.5 | 0.3 |
| 36.656 | 2.4496 | 3.7 | 2.1 |
| 37.167 | 2.4171 | 2.2 | 1.2 |
| 38.281 | 2.3493 | 3.0 | 1.7 |
| 38.573 | 2.3322 | 0.9 | 0.5 |
| 38.966 | 2.3095 | 6.5 | 3.6 |
| 39.488 | 2.2802 | 1.1 | 0.6 |
| 39.622 | 2.2728 | 1.5 | 0.8 |

Significant peaks are bolded.

Example 4

Sodium Thiosulfate Binding Capacity Assay

A high performance liquid chromatography ultra-violet spectroscopy (HPLC-UV) assay was developed to quantitate the binding capacity of thiosulfate for cisplatin. This method permits comparison of the binding capacity of different lots of sodium thiosulfate or pharmaceutical compositions containing sodium thiosulfate. The HPLC-UV method directly measures the diminution of cisplatin over time in the presence of varying concentrations of sodium thiosulfate.

The method uses a Waters Acquity H-Class HPLC system with an Imtakt Scherzo SW-C18 mixed mode column. The HPLC method conditions are outlined in Table 7. The method has a linear response covering cisplatin concentrations from 3.3 μM (0.001 mg/mL) to 666 μM (0.2 mg/mL). This range covers greater than two orders of magnitude at dose-relevant concentrations.

TABLE 7

Sodium Thiosulfate HPLC-UV Method

HPLC System: Waters Acquity H-Class
Column: Imtakt Scherzo SW C18 Mixed-Mode, 150 mm × 3 mm, 3 μm
MPA: 0.5 mM Ammonium formate in 9:1 $H_2O$:Acetonitrile, pH 4
MPB: 200 mM Ammonium formate in 7:3 $H_2O$:Acetonitrile, pH 4
Detection: UV 220 nm
Column Temperature: 35° C.
Diluent: 0.9% NaCl in $H_2O$
Flow Rate: 0.4 mL/min

| Gradient Conditions | | |
|---|---|---|
| Time (min) | MPA (%) | MPB (%) |
| 0 | 100 | 0 |
| 3 | 100 | 0 |
| 4.5 | 90 | 10 |
| 6.5 | 90 | 10 |
| 6.6 | 100 | 0 |
| 10.0 | 100 | 0 |

The assay was performed by mixing equal volumes containing 333 μM, 400 μM, or 666 μM of sodium thiosulfate with 666 μM cisplatin (ratios of 5:1, 6:1, or 10:1 thiosulfate:cisplatin, respectively). Each sample was transferred to an HPLC vial and placed in an autosampler chamber held at 24° C. Samples were injected onto the HPLC system approximately every 30 minutes to obtain 4 time-points for each sample. A gradient was run and the retention time and peak area were obtained. The decrease in concentration of cisplatin was monitored over time to obtain a reaction rate (e.g., the slope of the line, [cisplatin]/min) and calculated half-life (the time to reach 333/2 μM cisplatin based on the slope of the line). Control samples contained 333 μM cisplatin.

Exemplary results are summarized in Table 8 and FIG. 4.

TABLE 8

Sodium Thiosulfate-Cisplatin Binding Assay Results
Cisplatin Concentration (μM)

| Time (min) | Cntrl | Cntrl | Cntrl | 5:1 | 5:1 | 6:1 | 6:1 | 10:1 | 10:1 |
|---|---|---|---|---|---|---|---|---|---|
| 4 | 328.7 | 333.1 | 328.1 | 323.7 | 323.7 | | | 319.5 | |
| 5 | | | | | | 325.4 | 324.5 | | 320.3 |
| 37 | 317.9 | 322.3 | 316.3 | 294.2 | 294.0 | | | 269.4 | |
| 38 | | | | | | 286.4 | 293.2 | | 278.5 |
| 70 | 295.4 | 308.6 | 303.6 | 266.8 | 268.0 | | | 235.2 | |
| 71 | | | | | | 259.8 | 266.2 | | 239.6 |
| 103 | 286.9 | 296.6 | 292.5 | 243.7 | 245.3 | | | 205.6 | |
| 104 | | | | | | 235.6 | 240.5 | | 209.3 |

| Linear Regression of Cisplatin Conc. vs. Time | | | | |
|---|---|---|---|---|
| | Control (n = 3) | 5:1 (n = 2) | 6:1 (n = 2) | 10:1 (n = 2) |
| Slope (Cisplatin Area/min) | −0.40 | −0.80 | −0.87 | −1.13 |

TABLE 8-continued

Sodium Thiosulfate-Cisplatin Binding Assay Results
Cisplatin Concentration (μM)

| | | | | |
|---|---|---|---|---|
| $R^2$ | 0.99 | 1.00 | 0.99 | 0.99 |
| y-int | 332 | 325 | 326 | 321 |
| Half-life (min) | 423 | 198 | 184 | 136 |

Example 5

Formulation Preparation

Figure 5:
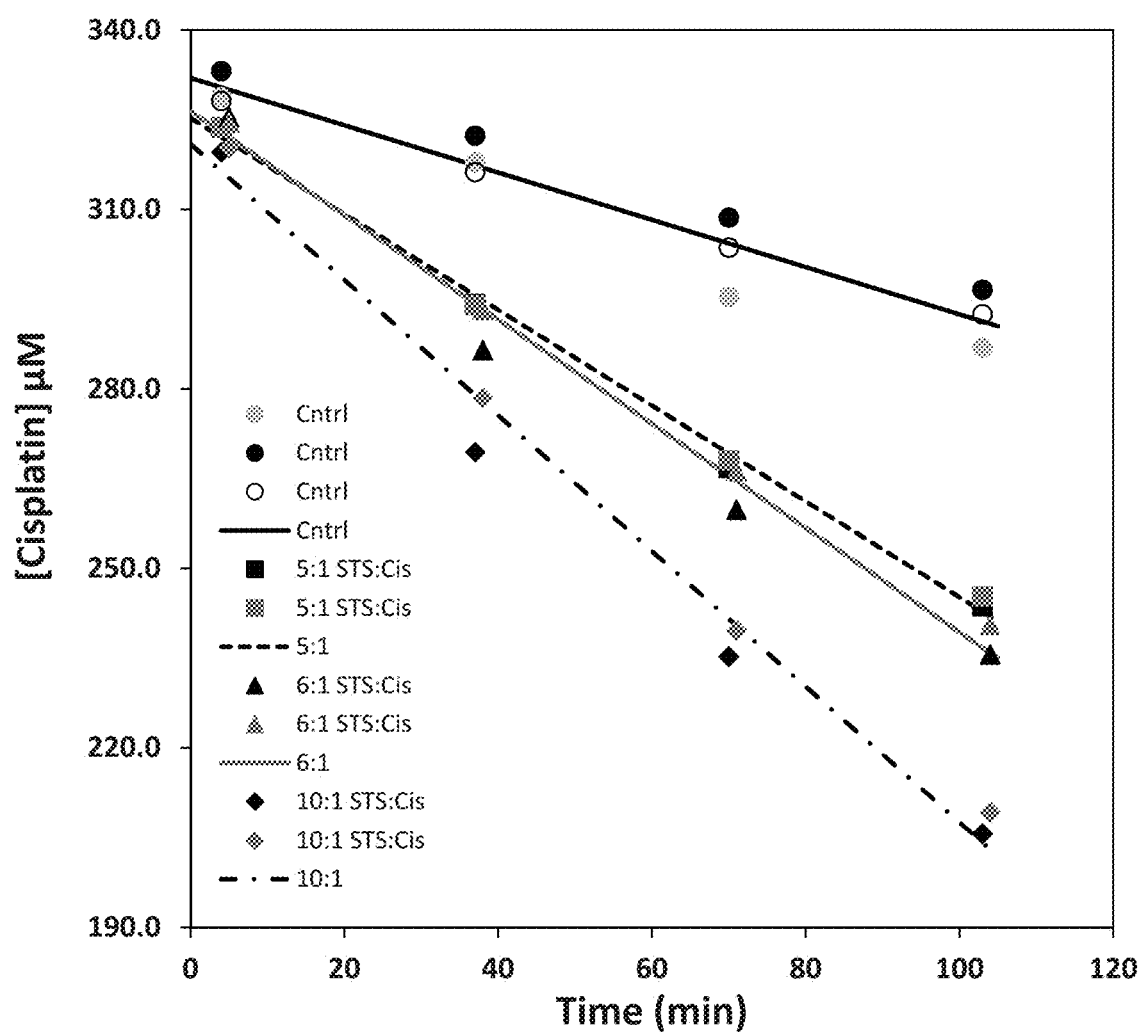
FIG. 5 shows a plot of cisplatin concentration versus time for cisplatin (control) or cisplatin combined with sodium thiosulfate at ratios of sodium thiosulfate:cisplatin of 5:1, 6:1, or 10:1. Data are shown in Table 7.
Figure 6:
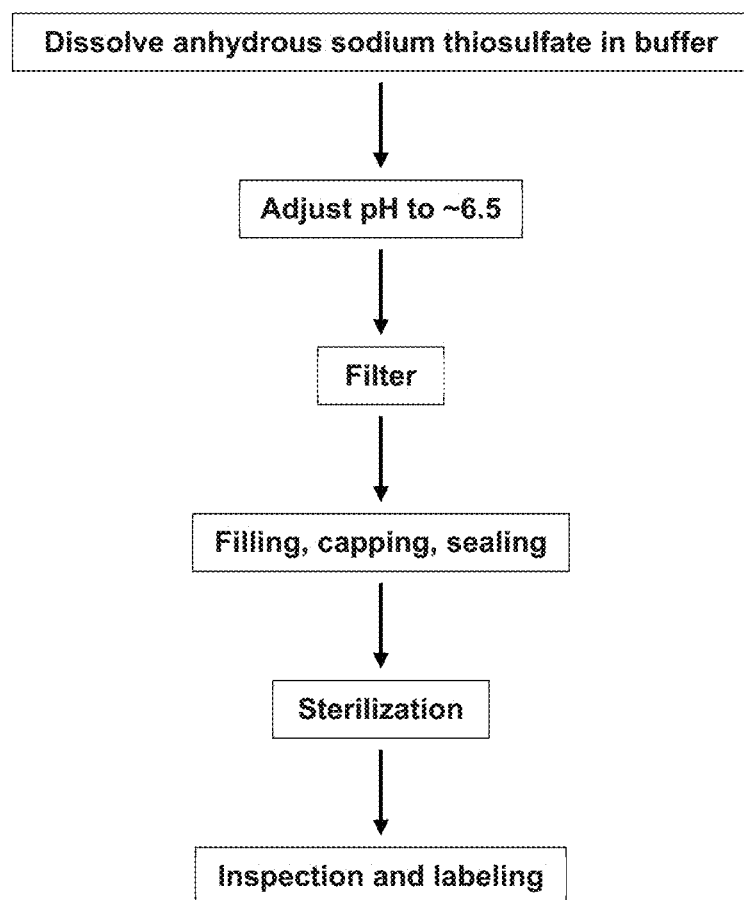
FIG. 6 shows a scheme for preparing a pharmaceutical formulation comprising anhydrous sodium thiosulfate.

The process for preparing the sodium thiosulfate formulation is shown in FIG. 5. Anhydrous sodium thiosulfate was dissolved in sodium phosphate buffer (~10 mM sodium phosphate). An exemplary sodium thiosulfate pharmaceutical formulation is shown in Table 9. The pH was adjusted to ca. 6.5 with NaOH and HCl or phosphoric acid. The solution was filtered twice through 0.22 μm filters. The filtered solution was filled into glass vials. The vials were sealed with septa and crimped. The sealed filled vials were autoclaved at 121° C., 15 psi for at least 0.5 h to sterilize the contents. The vials were inspected, labeled, and stored at ambient temperature.

TABLE 9

Exemplary Sodium Thiosulfate Formulation

| Component | Mass/Volume | Molarity |
|---|---|---|
| Sodium thiosulfate, anhydrous | 80.0 mg/mL | 0.5 M |
| Sodium phosphate, monobasic, monohydrate | 1.23 mg/mL | 0.0087 M |
| Sodium phosphate, dibasic, anhydrous | 0.16 mg/mL | 0.0012 M |
| Total phosphate buffer | 1.39 mg/mL | 0.01 M |
| Hydrochloric acid | q.s. | q.s. |
| Sodium hydroxide | q.s. | q.s. |
| Final pH: 7.0-8.0 | | |

Example 6

The manufacturing process for anhydrous sodium thiosulfate as described herein comprises the following steps:

Step 1: Chemical synthesis of sodium thiosulfate, aqueous;
Step 2: Crystallization of sodium thiosulfate (wet) and washing with acetone;
Step 3: Dehydration and isolation of anhydrous sodium thiosulfate; and
Step 4: Packaging.

The synthesis route is presented in Scheme II and each step is described further below.

Scheme II

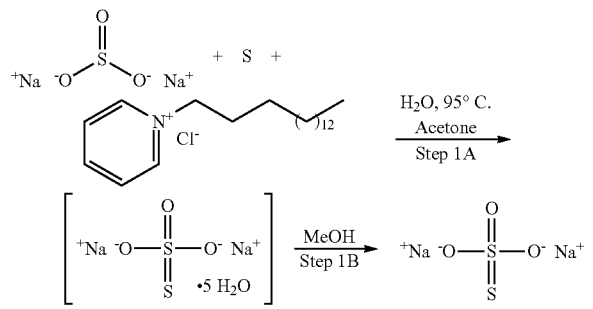

Synthesis of Sodium Thiosulfate

The synthesis of aqueous sodium thiosulfate was accomplished by reacting 1.0 mole equivalents of aqueous sodium sulfite with 1.1 mole equivalents of solid elemental sulfur (trace metals) under aqueous conditions at 95±5° C. in the presence of catalytic amounts of cetylpyridinium chloride (0.00013 mole equivalents) to form sodium thiosulfate. See Scheme II. The reaction completeness was verified after 6 hours by measuring the amount of residual sodium sulfite present (e.g., <0.15% w/w sulfite by HPLC-CAD). The finished reaction was then cooled to 20±5° C. for at least 3 hours and held at 20±5° C. for at least 1 hour. The product solution was passed through a 1 μm bag filter followed by a 0.45 μm cartridge polishing filter to remove any residual sulfur while transferring the product to a crystallization vessel.

Crystallization of Sodium Thiosulfate (Wet)

The product solution was cooled in a crystallization vessel to 0±5° C. with vigorous agitation, and about 35% of the total acetone was added and mixed for at least 20 min while maintaining a temperature of no more than 10° C. After incubation at 0±5° C. for about 5 to about 20 min, a sodium thiosulfate seed crystal was added and the crystallization was performed at 0±5° C. for about 5 to about 20 min. The remaining quantity of acetone was added while the temperature was maintained at 0±5° C. The slurry was then held at 0±5° C. for at least 0.5 hour and then transferred to a filter dryer. The filtrate was removed by pressure filtration. The slurry was filtered to the point where the filtrate drops just below the level of the cake after each portion of slurry was added; this process minimized cracking of the resulting cake. The cake was then washed twice with acetone and blown with $N_2$ gas until no liquid exited. The resulting cake of "wet sodium thiosulfate" was then dried at ambient temperature and atmospheric pressure with $N_2$ blowing through the cake for at least 1 hour. The term "wet sodium thiosulfate" or "sodium thiosulfate (wet)" as used herein refers to sodium thiosulfate that has not been dehydrated.

Dehydration and Isolation of Anhydrous Sodium Thiosulfate

Filtered methanol, heated to 60±5° C. was charged into the filter dryer containing the dried "wet" sodium thiosulfate material and agitated continuously at 45±5° C. for at least 3 hours. The material was blown with nitrogen for at least 2 hours. The temperature was then raised to 55±5° C. and the solid is dried under vacuum for at least 24 hours. Afterwards, the residual solvents were tested using gas chromatography for volatile impurities. The anhydrous sodium thiosulfate material was cooled to 20±5° C. under slight nitrogen pressure.

Packaging

Immediately after cooling, the anhydrous sodium thiosulfate drug substance was transferred into HDPE drums that were double lined with LDPE bags and contained a desiccant between the LDPE liners. The drums were purged with nitrogen gas prior to sealing.

Manufacturing specifications are shown in Table 10.

TABLE 10

Anhydrous Sodium Thiosulfate Manufacturing Specifications

Section I: General Information

| | | | |
|---|---|---|---|
| Name | Sodium Thiosulfate Anhydrous | Specification Classification | Drug Substance |
| Molecular Weight | 158.11 g/mol | Structure | |
| Storage Condition | Room Temperature (25° C.) | Retest Date | 12 months from manufacture |
| Bulk Primary Storage Container | HDPE Keg with Heat-sealed foil pouch containing double-lined poly bag with desiccant | Sample Container(s) | Heat-sealed foil pouch containing double-lined poly bag with desiccant |
| Test Sample Amount | Release: 5 grams MET: 15 grams | Retention Sample Amount | N/A |

Section II: Testing Attributes and Methods

| Test | Method | Attribute | Specification (Limit/Range/Description) |
|---|---|---|---|
| Appearance | Internal | Appearance | White to off-white solid, free of particulates |
| Identification by FTIR | cUSP (197A) | Identification conforms to reference spectrum | |
| Identification | cUSP Sodium (191) | Identification meets the requirements | |
| Identification by IC | Internal | Identification | Retention time of Thiosulfate in sample corresponds to that of reference standard |
| Impurities by HPLC | Internal | Residual Sulfite | NMT 0.5% |
| | | Residual Sulfate | NMT 1.5% |
| Assay by IC | Internal | Assay, solvent free and anhydrous basis | 97.5-102.5% |

NMT not more than.

The following pages show manufacturing specifications of anhydrous sodium thiosulfate produced by the method described above in 10 kg and 30 kg batches (Tables 11 and 12).

TABLE 11

Specifications for Anhydrous Sodium Thiosulfate Manufactured at 10 kg Scale

| Test | Method | Specification | 1-A | 1-B | 1-C | 1-D |
|---|---|---|---|---|---|---|
| Appearance | Visual | White to off-white solid, free of particulates | White to off-white solid, free of particulates | White to off-white solid, free of particulates | White to off-white solid, free of particulates | White to off-white solid, free of particulates |
| Identification by FTIR | cUSP <197A> | Conforms to reference spectrum | Conforms | Conforms | Conforms | Conforms |
| Identification | cUSP Sodium <191> | Meets the requirements | Present | Present | Present | Present |
| Identification by IC | Ion chromatography | Retention time of Thiosulfate in sample corresponds to that of reference standard | Conforms | Conforms | Conforms | Conforms |
| Assay by IC | Ion chromatography | 97.5-102.5% (as is) | 99.1% | 101.1% | 101.3% | 100.4% |
| Impurities by IC | Ion chromatography | Residual Sulfite: NMT 0.15% | Sulfite: ND | Sulfite: ND | Sulfite: ND | Sulfite: ND |
| | | Residual Sulfate: NMT 1.5% | Sulfate: 0.56% | Sulfate: 0.56% | Sulfate: 0.54% | Sulfate: 0.6% |

TABLE 11-continued

Specifications for Anhydrous Sodium Thiosulfate Manufactured at 10 kg Scale

| | | | | | | |
|---|---|---|---|---|---|---|
| Water Content | Karl Fischer USP <921> 1c | NMT 3.0% (w/w) | 0.1% | 0.1% | 0.1% | 0.1% |
| OVI by GC | GC | Acetone: ≤2500 ppm Methanol: ≤1500 ppm | Acetone: ND MeOH: ND | Acetone: <100 ppm MeOH: <100 ppm | Acetone: <100 ppm MeOH: <100 ppm | Acetone: ND MeOH: ND |
| Polymorphic Form | XRPD | Sample pattern conforms with reference spectrum | Conforms | Conforms | Conforms | Conforms |
| Elemental Impurities or Elemental Limit Analysis | ICP-MS | Cd: ≤0.1 ppm Pb: ≤0.25 ppm As: ≤0.75 ppm Hg: ≤0.15 ppm Co: ≤0.25 ppm V: ≤0.5 ppm Ni: ≤1 ppm Li: ≤12.5 ppm Sb: ≤4.5 ppm Cu: ≤15.0 ppm | Cd: <0.05 Pb: <0.125 As: <0.375 Hg: <0.075 Co: <0.125 V: <0.25 Ni: <0.5 Li: <2.25 Sb: <6.25 Cu: <7.5 | Cd: <0.05 Pb: <0.125 As: <0.375 Hg: <0.075 Co: <0.125 V: <0.25 Ni: <0.5 Li: <2.25 Sb: <6.25 Cu: <7.5 | Cd: <0.05 Pb: <0.125 As: <0.375 Hg: <0.075 Co: <0.125 V: <0.25 Ni: <0.5 Li: <2.25 Sb: <6.25 Cu: <7.5 | Cd: <0.05 Pb: <0.125 As: <0.375 Hg: <0.075 Co: <0.125 V: <0.25 Ni: <0.5 Li: <2.25 Sb: <6.25 Cu: <7.5 |
| Microbial Enumeration Tests | USP <61> | Total Aerobic Microbial Count: ≤100 cfu/g | 2 CFU/g | <1 CFU/g | 3 CFU/g | <1 CFU/g |
| | | Total Yeasts and Molds Count: ≤100 cfu/g | <1 CFU/g | <1 CFU/g | <1 CFU/g | <1 CFU/g |
| Endotoxin | USP <85> | NMT 5.0 EU/g | <0.5 EU/g | <0.5 EU/g | <0.5 EU/g | <0.5 EU/g |

| Test | Method | Specification | 1-E | 1-F | 2-A | 2-B |
|---|---|---|---|---|---|---|
| Appearance | Visual | White to off-white solid, free of particulates | White to off-white solid, free of particulates | White to off-white solid, free of particulates | White to off-white solid, free of particulates | White to off-white solid, free of particulates |
| Identification by FTIR | cUSP <197A> | Conforms to reference spectrum | Conforms | Conforms | Conforms | Conforms |
| Identification | cUSP Sodium <191> | Meets the requirements | Present | Present | Present | Present |
| Identification by IC | Ion chromatography | Retention time of Thiosulfate in sample corresponds to that of reference standard | Conforms | Conforms | Conforms | Conforms |
| Assay by IC | Ion chromatography | 97.5-102.5% (as is) | 99.3% | 99.5% | 99.9% | 101.2% |
| Impurities by IC | Ion chromatography | Residual Sulfite: NMT 0.15% | Sulfite: ND | Sulfite: ND | Sulfite: ND | Sulfite: ND |
| | | Residual Sulfate: NMT 1.5% | Sulfate: 0.6% | Sulfate: 0.55% | Sulfate: 0.55% | Sulfate: 0.52% |
| Water Content | Karl Fischer USP <921> 1c | NMT 3.0% (w/w) | 0.1% | 0.0% | 0.1% | 0.04% |
| OVI by GC | GC | Acetone: ≤2500 ppm Methanol: ≤1500 ppm | Acetone: ND MeOH: ND | Acetone: ND MeOH: ND | Acetone: ND MeOH: ND | Acetone: ND MeOH: ND |
| Polymorphic Form | XRPD | Sample pattern conforms with reference spectrum | Conforms | Conforms | Conforms | Conforms |
| Elemental Impurities or Elemental Limit Analysis | ICP-MS | Cd: ≤0.1 ppm Pb: ≤0.25 ppm As: ≤0.75 ppm Hg: ≤0.15 ppm Co: ≤0.25 ppm V: ≤0.5 ppm Ni: ≤1 ppm | Cd: <0.05 Pb: <0.125 As: <0.375 Hg: <0.075 Co: <0.125 V: <0.25 Ni: <0.5 | Cd: <0.05 Pb: <0.125 As: <0.375 Hg: <0.075 Co: <0.125 V: <0.25 Ni: <0.5 | Cd: <0.05 Pb: <0.125 As: <0.375 Hg: <0.075 Co: <0.125 V: <0.25 Ni: <0.5 | Cd: <0.05 Pb: <0.125 As: <0.375 Hg: <0.075 Co: <0.125 V: <0.25 Ni: <0.5 |

TABLE 11-continued

Specifications for Anhydrous Sodium Thiosulfate Manufactured at 10 kg Scale

|  |  |  |  |  |  |  |
|---|---|---|---|---|---|---|
|  |  | Li: ≤12.5 ppm<br>Sb: ≤4.5 ppm<br>Cu: ≤15.0 ppm | Li: <2.25<br>Sb: <6.25<br>Cu: <7.5 | Li: <2.25<br>Sb: <6.25<br>Cu: <7.5 | Li: <2.25<br>Sb: <6.25<br>Cu: <7.5 | Li: <2.25<br>Sb: <6.25<br>Cu: <7.5 |
| Microbial<br>Enumeration<br>Tests | USP <61> | Total Aerobic<br>Microbial<br>Count: ≤100<br>cfu/g | <1 CFU/g | <1 CFU/g | <1 CFU/g | <1 CFU/g |
|  |  | Total Yeasts<br>and Molds<br>Count: ≤100<br>cfu/g | <1 CFU/g | <1 CFU/g | <1 CFU/g | <1 CFU/g |
| Endotoxin | USP <85> | NMT 5.0 EU/g | <0.5 EU/g | <0.5 EU/g | <0.5 EU/g | <0.5 EU/g |

NMT: not more than.

TABLE 12

Specifications for Anhydrous Sodium Thiosulfate Manufactured at 30 kg Scale

| Test | Method | Specification | 1 | 2 | 3 |
|---|---|---|---|---|---|
| Appearance | Visual | White to off-white solid, free of particulates | White solid, free of particulates | White solid, free of particulates | White to off-white solid, free of particulates |
| Identification by FTIR | cUSP (197A) | Conforms to reference spectrum | Conforms | Conforms | Conforms |
| Identification | cUSP Sodium (191) | Meets the requirements | Present | Present | Present |
| Identification by IC | Ion chromatography | Retention time of Thiosulfate in sample corresponds to that of reference standard | Conforms | Conforms | Conforms |
| Assay by IC | Ion chromatography | 97.5-102.5% (as is) | 98.9% | 98.3% | 98.1% |
| Impurities by IC | Ion chromatography | Residual Sulfite: NMT 0.15%<br>Residual Sulfate: NMT 1.5% | Sulfite: ND<br>Sulfate: 0.9% | Sulfite: ≤0.10%<br>Sulfate: 1.0% | Sulfite: ND<br>Sulfate: 0.9% |
| Water Content | Karl Fischer USP (921) 1c | NMT 3.0% (w/w) | 0.0% | 0.1% | 0.0% |
| OVI by GC | GC | Acetone: ≤2500 ppm<br>Methanol: ≤1500 ppm | Acetone: ND<br>MeOH: ≤100 ppm | Acetone: ND<br>MeOH: 133 ppm | Acetone: ND<br>MeOH: 238 ppm |
| Polymorphic Form | XRPD | Sample pattern conforms with reference spectrum | Conforms | Conforms | Conforms |
| Elemental Impurities or Elemental Limit Analysis | ICP-MS | Cd: ≤0.1 ppm<br>Pb: ≤0.25 ppm<br>As: ≤0.75 ppm<br>Hg: ≤0.15 ppm<br>Co: ≤0.25 ppm<br>V: ≤0.5 ppm<br>Ni: ≤1 ppm<br>Li: ≤12.5 ppm<br>Sb: ≤4.5 ppm<br>Cu: ≤15.0 ppm |  |  |  |
| Microbial Enumeration Tests | USP (61) | Total Aerobic Microbial Count: ≤100 cfu/g<br>Total Yeasts and Molds Count: ≤100 cfu/g | ≤1 CFU/g<br>≤1 CFU/g | ≤1 CFU/g<br>≤1 CFU/g | ≤1 CFU/g<br>≤1 CFU/g |
| Endotoxin | USP (85) | NMT 5.0 EU/g | ≤0.5 CFU/g | ≤0.5 CFU/g | ≤0.5 CFU/g |

ND Not determined;
NMT not more than.

Example 7

Figure 4A:
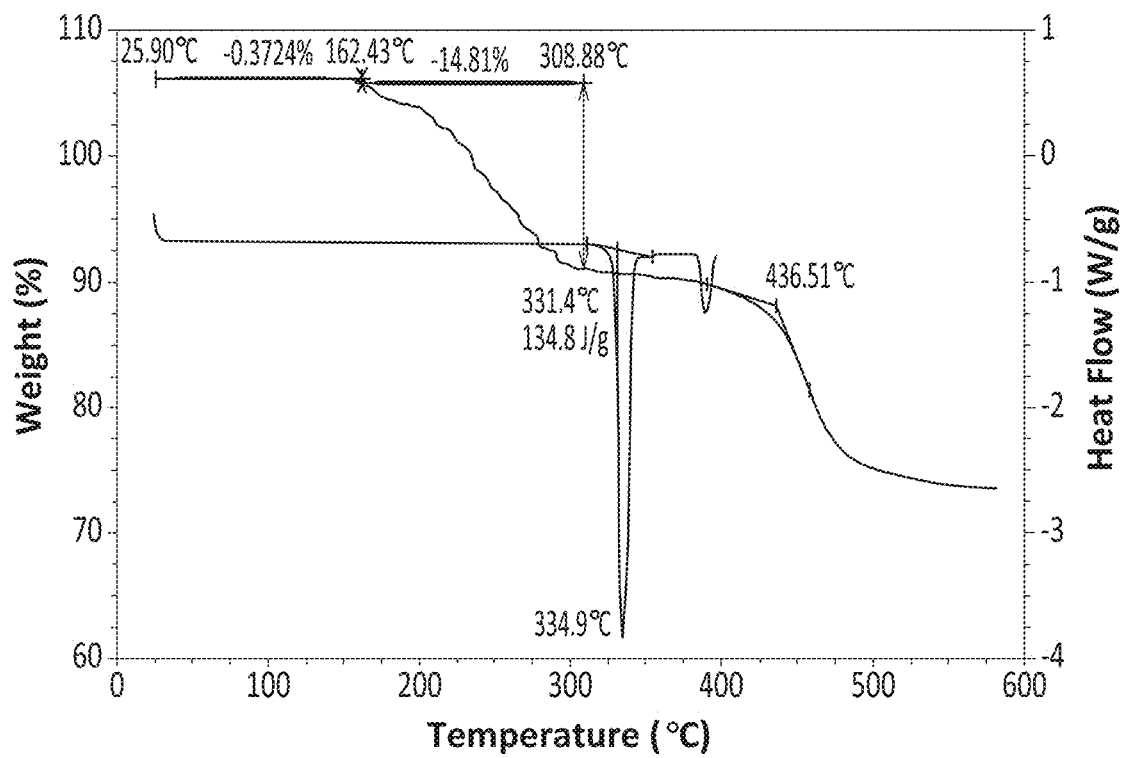
FIG. 4A shows overlayed differential scanning calorimetry (DSC) and thermogravimetric analysis (TGA) for anhydrous sodium thiosulfate synthesized as described herein. The DSC thermogram shows a single, sharp endotherm with an onset of 331.4° C. In the thermogravimetric analysis, there is negligible weight loss from 25° C. to 162° C.; from 162° C. to 309° C. there is a weight loss of 14.81% followed by the onset of decomposition at 436° C.
Figure 4B:
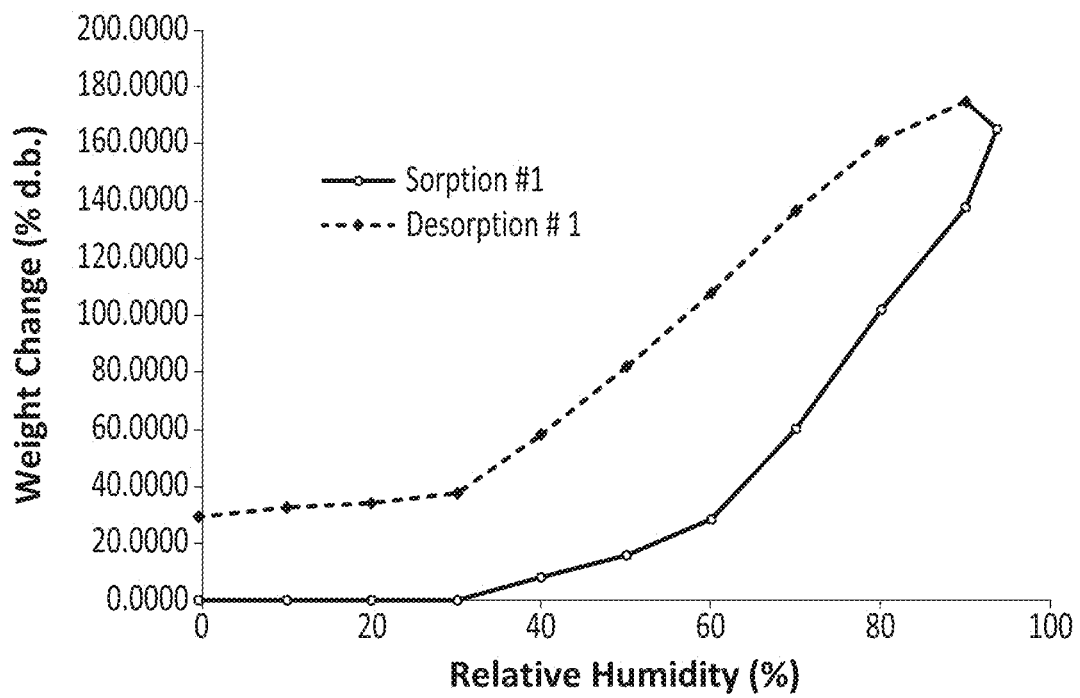
FIG. 4B shows the dynamic vapor sorption (DVS) isotherm for anhydrous sodium thiosulfate synthesized as described herein. The DVS isotherm showed a minimal weight change upon equilibration to 0% relative humidity. Upon sorption, the exhibits a weight gain of 165%. Hysteresis was observed upon desorption, with a weight loss of 51%.

The anhydrous sodium thiosulfate synthesized as described herein is a crystalline material that exhibits sharp XRPD peaks (FIG. 2A) and birefringent particles with blade- and plate-like crystal morphology. Thermal analysis by differential scanning calorimetry (DSC) showed a single, sharp endotherm with an onset of 331.4° C. that is the apparent melting temperature (FIG. 4A). In the thermogravimetric analysis (TGA), there was negligible weight loss from ambient temperature to 162° C. From 162° C. to 309° C., there was a weight loss of 14.81% followed by an onset of decomposition at 436° C. (FIG. 4A). The dynamic vapor sorption (DVS) isotherm showed a minimal weight change upon equilibration to 0% relative humidity (FIG. 4B). Upon sorption, the exhibits a weight gain of 165%. Hysteresis was observed upon desorption, with a weight loss of 51%.

By comparison, the DSC thermogram of sodium thiosulfate pentahydrate showed multiple endothermic events with maxima at 56, 111, 131, and 141° C., with a melt onset at 331° C. A 45.33% weight loss was observed in TGA from 25° C. until −300° C., followed by decomposition at 456° C. The DVS isotherm showed a 27% weight loss upon drying. The material had a weight gain of 81% upon sorption. Hysteresis was observed upon desorption, with a weight loss of 51%.

Example 8

A process for preparing the sodium thiosulfate formulation for injection is shown in FIG. 5. Anhydrous sodium thiosulfate was dissolved in borate buffer (~4 mM boric acid). An exemplary sodium thiosulfate pharmaceutical formulation is shown in Table 13. The pH was adjusted to ca. 8.6-8.8 with NaOH and HCl. The solution was filtered twice through 0.22 μm filters. The filtered solution was filled into glass vials. The vials were sealed with septa, aluminum rings, and crimped. The sealed filled vials were autoclaved at 121° C., 15 psi for at least 0.5 h to sterilize the contents. The vials were inspected, labeled, and stored at ambient temperature.

TABLE 13

Exemplary Sodium Thiosulfate Formulation

| Component | Mass/Volume | Molarity |
|---|---|---|
| Sodium thiosulfate, anhydrous | 80.0 mg/mL | 0.5 M |
| Boric acid | 0.25 mg/mL | 0.004 M |
| Hydrochloric acid | q.s. | q.s. |
| Sodium hydroxide | q.s. | q.s. |
| Final pH: 8.6-8.8 | | |

Table 14 shows the manufacturing specifications for the sodium thiosulfate formulation for injection.

TABLE 14

Sodium Thiosulfate For Injection Drug Product Specifications

| Parameters | Method/Laboratory | Acceptance Criteria |
|---|---|---|
| Appearance | Visual | Clear, colorless solution essentially free of particulate matter |
| Identification: Thiosulfate | HPLC | Retention time of thiosulfate in sample agrees with retention time of reference material |
| Clarity and Degree of Opalescence of Liquids | Ph. Eur. 2.2.1 | NMT Reference suspension 1 |
| Degree of Coloration of a Liquid | Ph. Eur. 2.2.2 | |
| Identification STS by FTIR | USP (197) | Conforms to reference spectrum |
| Identification for Sodium | US (191) | Meets requirements |
| pH | USP (791) Ph. Eur. 2.2.3 | 7.0-9.0 |
| Assay | IC | US Release: 90.0-110.0% label claim Stability: 90.0-110.0% label claim EU Release: 95.0-105.0% label claim Stability: 90-100.0% lable claim |
| Sulfite | IC | NMT 0.15% |
| Sulfate | IC | NMT 1.5% |
| Sulfur | HPLC-UV | NMT 0.15% |
| Extractable Volume | USP (1) Ph. Eur 2.9.17 | NLT 100 mL |
| Particulate Matter | USP (788) Ph. Eur. 2.9.19 | 10 μm: ≤3000 25 μm: ≤3000 |
| Sterility | USP (71) Ph. Eur. 2.6.1 | No growth observed |
| Bacterial Endotoxin | USP (85) | |

NMT not more than

Example 9

Exemplary sodium thiosulfate pharmaceutical formulations are shown in Tables 15-23. These formulations are prepared as described herein.

TABLE 15

Exemplary Sodium Thiosulfate Formulation

| Component | Mass/Volume | Molarity |
|---|---|---|
| Sodium thiosulfate, anhydrous | 80.0 mg/mL | 0.5 M |
| Sodium phosphate, monobasic, monohydrate | 1.23 mg/mL | 0.0012 M |
| Sodium phosphate, dibasic, anhydrous | 0.16 mg/mL | 0.0087 M |
| Total phosphate buffer | 1.39 mg/mL | 0.01 M |
| Hydrochloric acid | q.s. | q.s. |
| Sodium hydroxide | q.s. | q.s. |
| Final pH: 7.5-8.0 | | |

TABLE 16

Exemplary Sodium Thiosulfate Formulation

| Component | Mass/Volume | Molarity |
|---|---|---|
| Sodium thiosulfate, anhydrous | 80.0 mg/mL | 0.5 M |
| Sodium phosphate, monobasic, monohydrate | 2.46 mg/mL | 0.017 M |
| Sodium phosphate, dibasic, anhydrous | 0.31 mg/mL | 0.0023 M |
| Total phosphate buffer | 2.77 mg/mL | 0.02 M |
| Hydrochloric acid | q.s. | q.s. |
| Sodium hydroxide | q.s. | q.s. |
| Final pH: 7.5-8.0 | | |

TABLE 17

Exemplary Sodium Thiosulfate Formulation

| Component | Mass/Volume | Molarity |
|---|---|---|
| Sodium thiosulfate, anhydrous | 80.0 mg/mL | 0.5 M |
| Boric acid | 0.25 mg/mL | 0.004 M |
| Hydrochloric acid | q.s. | q.s. |
| Sodium hydroxide | q.s. | q.s. |
| Final pH: 8.6-8.8 | | |

TABLE 18

Exemplary Sodium Thiosulfate Formulation

| Component | Mass/Volume | Molarity |
|---|---|---|
| Sodium thiosulfate, anhydrous | 80.0 mg/mL | 0.5 M |
| Glycine | 1.5 mg/mL | 0.02 M |
| Hydrochloric acid | q.s. | q.s. |
| Sodium hydroxide | q.s. | q.s. |
| Final pH: 8.5-8.9 | | |

TABLE 19

Exemplary Sodium Thiosulfate Formulation

| Component | Mass/Volume | Molarity |
|---|---|---|
| Sodium thiosulfate, anhydrous | 80.0 mg/mL | 0.5 M |
| Glycine | 2.3 mg/mL | 0.03 M |
| Hydrochloric acid | q.s. | q.s. |
| Sodium hydroxide | q.s. | q.s. |
| Final pH: 8.5-8.9 | | |

TABLE 20

Exemplary Sodium Thiosulfate Formulation

| Component | Mass/Volume | Molarity |
|---|---|---|
| Sodium thiosulfate, anhydrous | 80.0 mg/mL | 0.5 M |
| Glycine | 3.8 mg/mL | 0.05 M |
| Hydrochloric acid | q.s. | q.s. |
| Sodium hydroxide | q.s. | q.s. |
| Final pH: 8.5-8.9 | | |

TABLE 21

Exemplary Sodium Thiosulfate Formulation

| Component | Mass/Volume | Molarity |
|---|---|---|
| Sodium thiosulfate, anhydrous | 80.0 mg/mL | 0.5 M |
| Tris(hydroxymethyl)aminomethane (Tromethane) | 1.21 mg/mL | 0.01 M |
| Hydrochloric acid | q.s. | q.s. |
| Sodium hydroxide | q.s. | q.s. |
| Final pH: 8.5-8.9 | | |

TABLE 22

Exemplary Sodium Thiosulfate Formulation

| Component | Mass/Volume | Molarity |
|---|---|---|
| Sodium thiosulfate, anhydrous | 80.0 mg/mL | 0.5 M |
| Tris(hydroxymethyl)aminomethane (Tromethane) | 2.42 mg/mL | 0.02 M |
| Hydrochloric acid | q.s. | q.s. |
| Sodium hydroxide | q.s. | q.s. |
| Final pH: 8.5-8.9 | | |

TABLE 23

Exemplary Sodium Thiosulfate Formulation

| Component | Mass/Volume | Molarity |
|---|---|---|
| Sodium thiosulfate, anhydrous | 80.0 mg/mL | 0.5 M |
| Tris(hydroxymethyl)aminomethane (Tromethane) | 3.63 mg/mL | 0.03 M |
| Hydrochloric acid | q.s. | q.s. |
| Sodium hydroxide | q.s. | q.s. |
| Final pH: 8.5-8.9 | | |

What is claimed:

1. A pharmaceutical composition comprising aqueous anhydrous sodium thiosulfate, wherein the aqueous anhydrous sodium thiosulfate is at a concentration of about 0.5 M and further comprising about 0.004 M boric acid.

2. The pharmaceutical composition of claim 1, wherein the pharmaceutical composition has a total volume of about 100 mL.

3. The pharmaceutical composition of claim 1, wherein the pharmaceutical composition further comprises hydrochloric acid.

4. The pharmaceutical composition of claim 2, wherein the pharmaceutical composition further comprises hydrochloric acid.

5. The pharmaceutical composition of claim 1, wherein the pharmaceutical composition further comprises sodium hydroxide.

6. The pharmaceutical composition of claim 2, wherein the pharmaceutical composition further comprises sodium hydroxide.

7. The pharmaceutical composition of claim 1, wherein the pharmaceutical composition has a pH between about 5 and about 9.5.

8. The pharmaceutical composition of claim 1, wherein the pharmaceutical composition has a pH between about 6.5 and about 8.9.

9. The pharmaceutical composition of claim 1, wherein the pharmaceutical composition has a pH between about 8.6 and about 8.8.

* * * * *

UNITED STATES PATENT AND TRADEMARK OFFICE
CERTIFICATE OF CORRECTION

PATENT NO. : 11,291,728 B2  
APPLICATION NO. : 17/005997  
DATED : April 5, 2022  
INVENTOR(S) : Smith Page 1 of 1

It is certified that error appears in the above-identified patent and that said Letters Patent is hereby corrected as shown below:

On the Title Page

Item (12) delete "Lovelace et al." and insert -- Smith --

Item (72) Inventor(s): Thomas Claiborne Lovelace, Apex, NC (US)
    Joseph Alexander Moore III, Wake Forest, NC (US)
    Christopher McKinnon Lee, Holly Springs, NC (US)
    Daniel Logan Kirschner, Raleigh, NC (US)
Should be replaced with:
    Alexander Smith, Apex, NC (US)

Signed and Sealed this  
Twenty-seventh Day of August, 2024

Katherine Kelly Vidal  
*Director of the United States Patent and Trademark Office*